US012582481B2

(12) United States Patent 
Armiger et al.

(10) Patent No.: US 12,582,481 B2 
(45) Date of Patent: Mar. 24, 2026

(54) PREDICTIVE INTERNAL ANATOMY VISUALIZATION

(71) Applicant: The Johns Hopkins University, Baltimore, MD (US)

(72) Inventors: Robert S. Armiger, Catonsville, MD (US); Catherine M. Carneal, Silver Spring, MD (US); Nathan G. Drenkow, Columbia, MD (US); Nathanael P. Kuo, Laurel, MD (US); Connor O. Pyles, Columbia, MD (US); Anna E. Knight, Germantown, MD (US)

(73) Assignee: The Johns Hopkins University, Baltimore, MD (US)

( * ) Notice: Subject to any disclaimer, the term of this patent is extended or adjusted under 35 U.S.C. 154(b) by 175 days.

(21) Appl. No.: 18/647,311

(22) Filed: Apr. 26, 2024

(65) Prior Publication Data

US 2024/0358437 A1 Oct. 31, 2024

Related U.S. Application Data

(60) Provisional application No. 63/499,167, filed on Apr. 28, 2023.

(51) Int. Cl.
*G06T 7/33* (2017.01)
*A61B 34/00* (2016.01)
(Continued)

(52) U.S. Cl.
CPC ............ *A61B 34/10* (2016.02); *A61B 90/361* (2016.02); *G06T 7/344* (2017.01); *G06T 7/60* (2013.01);
(Continued)

(58) Field of Classification Search
CPC ........... G16H 40/63; G06T 7/344; G06T 7/60; G06T 7/73; G06T 19/006; G06T 19/20;
(Continued)

(56) References Cited

U.S. PATENT DOCUMENTS 10,832,486 B1 * 11/2020 Lo .......................... A61B 90/39

OTHER PUBLICATIONS

Lucio Tommaso De Paolis et al. Augmented Visualization With Depth Perception Cues To Improve The Surgeon's Performance In Minimally Invasive Surgery. Medical and Biological Engineering and Computing. vol. 57. pp. 995-1013 (2019).*

(Continued)

*Primary Examiner* — Jacinta M Crawford 
(74) *Attorney, Agent, or Firm* — Todd R. Farnsworth

(57) ABSTRACT

An anatomy visualization device may include a display, an optical sensor, and processing circuitry. The processing circuitry may be configured to capture, via the optical sensor, body registration points on a body of an individual, receive external anatomical measurements of the body, apply the external anatomical measurements to a body shape model, and determine an organ placement prediction for the body based on the application of external anatomical measurements to the body shape model. The organ placement prediction may include organ position information, organ size information, and organ shape information for a plurality of organs. The processing circuitry may also align the organ placement prediction with the body registration points and render, on the display, the organ placement prediction in alignment with the body registration points as an augmented reality object on the body.

20 Claims, 17 Drawing Sheets

(51) Int. Cl.

| | |
|---|---|
| *A61B 34/10* | (2016.01) |
| *A61B 90/00* | (2016.01) |
| *G06T 7/60* | (2017.01) |
| *G06T 7/73* | (2017.01) |
| *G06T 19/00* | (2011.01) |
| *G06T 19/20* | (2011.01) |
| *G16H 40/63* | (2018.01) |
| *A61B 90/50* | (2016.01) |

(52) U.S. Cl.
CPC .............. *G06T 7/73* (2017.01); *G06T 19/006* (2013.01); *G06T 19/20* (2013.01); *G16H 40/63* (2018.01); *A61B 2034/105* (2016.02); *A61B 2034/252* (2016.02); *A61B 2090/061* (2016.02); *A61B 2090/365* (2016.02); *A61B 2090/372* (2016.02); *A61B 2090/373* (2016.02); *A61B 2090/502* (2016.02); *G06T 2207/10132* (2013.01); *G06T 2207/30004* (2013.01); *G06T 2207/30196* (2013.01); *G06T 2210/41* (2013.01); *G06T 2219/2004* (2013.01)

(58) Field of Classification Search
CPC . G06T 2207/10132; G06T 2207/20081; G06T 2207/20084; G06T 2207/30004; G06T 2207/30196; G06T 2210/41; G06T 2219/2004; A61B 34/10; A61B 90/361; A61B 2034/105; A61B 2034/252; A61B 2090/061; A61B 2090/365; A61B 2090/372; A61B 2090/373; A61B 2090/502
USPC ........................................................ 345/633
See application file for complete search history.

(56) References Cited

OTHER PUBLICATIONS

Benish Fida et al. Augmented Reality In Open Surgery. Updates In Surgery. vol. 70. pp. 389-400 (2018).*

Von Haxthausen F., Moreta-Martinez R., Pose Díez De La Lastra A., Pascau J., Ernst F., UltrARsound: in situ visualization of live ultrasound images using Hololens 2., Int J Comput Assist Radiol Surg. Nov. 2022; 17(11):2081-2091, doi: 10.1007/s11548-022-02695-z, PMID: 35776399, PMCID, PMC9515035.

Nguyen T., Plishker W., Matisoff A., Sharma K., Shekhar R., Holous: Augmented reality visualization of live ultrasound images using HoloLens for ultrasound-guided procedures. International Journal of Computer Assisted Radiology and Surgery, Feb. 2022; 17(2):385-391. DOI: 10.1007/s11548-021-02526-7, PMID: 34817764.

Zhou, Y., Lelu, G., Labbé, B., Pasquier, G., Le Gargasson, P., Murienne, A., Launay, L., A Novel Augmented Reality Ultrasound Framework Using an RGB-D Camera and a 3D-printed Marker. arXiv preprint arXiv: 2205.04350, (2022).

Shao My., Vagg T., Seibold M., Doughty M., Towards a Low-Cost Monitor-Based Augmented Reality Training Platform for At-Home Ultrasound Skill Development. Journal of Imaging, 2022; 8 (11): 305, https://doi.org/10.3390/jimaging8110305.

Costa JN., Gomes-Fonseca J., Valente S., et al., Ultrasound training simulator using augmented reality glasses: an accuracy and precision assessment study, Annual International Conference, IEEE, Eng., Med. Biol. Socl, 2022, 2022:4461-4464.

Thabit A., Niessen WJ., Wolvius EB., Van Walsum T., Evaluation of marker tracking using mono and stereo vision in Microsoft HoloLens for surgical navigation. In: Linte CA, Siewerdsen JH, eds., Medical Imaging 2022, Image-Guided Procedures, Robotic Interventions, and Modeling. Vol. 12034, Society of Photo-Optical Instrumentation Engineers (SPIE) Conference Series; 2022:1203415, doi: 10.1117/12.2607262.

Guo, Z., Yu, H., Qin, Z., Xiao, W., Shen, Y., Lai, M., (2020) Augmented Reality Guidance System for Ultrasound-Guided Puncture Surgery Training, In: Kountchev, R., Patnaik, S., Shi, J., Favorskaya, M. (eds) Advances in 3D Image and Graphics Representation, Analysis, Computing and Information Technology, Smart Innovation, Systems and Technologies, vol. 180, Springer, Singapore. https://doi.org/10.1007/978-981-15-3867-4_28.

Rochlen L.R., Levine R., Tait A.R. First-Person Point-of-View-Augmented Reality for central-line insertion training: A usability and feasibility study, Simul. Healthcare 2017; 12:57-62, doi: 10.1097/SIH.0000000000000185.

Groves L., Li N., Peters TM., Chen Ecs., Towards a First-Person Perspective Mixed Reality Guidance System for Needle Interventions, J. Imaging, Jan. 8, 2022, 7.

ICT&Health, First Augmented Reality Solution For Hololens Cleared By The Fda, located at https://ictandhealth.com/first-augmented-reality-solution-for-hololens-cleared-by-the-fda/news/, Nov. 1, 2018, last accessed on Jun. 25, 2024.

Reynolds M., Augmented Reality Goggles give Surgeons X-ray Vision, located at: https://www.newscientist.com/article/2130678-augmented-reality-goggles-give-surgeons-x-rayvision/, May 11, 2017, last accessed on Aug. 26, 2024.

Dars A., 3D Augmented Reality Science Book Developed Using Panda3D SDK and PyPE, located at: https://www.researchgate.net/publication/319077557_3D_AUGMENTED_REALITY_SCIENCE_BOOK_DEVELOPED_USING_PANDA3D_SDK_AND_PyPE, Mar. 16, 2015, last accessed on Jun. 25, 2024.

Choi C., LiveScience, 'X-Ray Vision' T-Shirt Shows Inner Workings of the Human Body, located at: https://www.livescience.com/54091-virtual-reality-shirt-reveals-human-anatomy.html, Mar. 18, 2016, last accessed on Jun. 25, 2024.

Chiu et al., "Use of Deep-Learning Algorithm to Guide Novices in Performing Focused Assessment with Sonography in Trauma" JAMA Network Open. 2023;6(3):e235102. doi:10.1001/jamanetworkopen.2023.5102, Mar. 28, 2023.

Augmented Reality (AR) Surgical Navigation Solutions, Novarad, available at https://www.novarad.net/augmentedreality, last downloaded Jun. 25, 2024.

Condliffe J., AR Is Making Its Way into the OR, MIT Technology Review, available at: https://www.technologyreview.com/2017/05/11/151,744/ar-is-making-its-way-into-the-or/, May 11, 2017.

Munzer BW., Khan MM., Shipman B., Mahajan P., Augmented Reality in Emergency Medicine: A Scoping Review. Journal of Medical Internet Research, Apr. 17, 2019, 21, (4):e12368, doi: 10.2196/12368. PMID: 30994463; PMCID: PMC6492064.

Taye, G.D., Feleke, Y.A., Prediction of failures in the project management knowledge areas using a machine learning approach for software companies SN Applied Sciences, 2022 4(6), 165 doi: https://doi.org/10.1007/s42452-022-05051-7.

Leuze C., Zoellner A., Schmidt AR., Cushing RE., Fischer MJ., Joltes K., Zientara GP., Augmented reality visualization tool for the future of tactical combat casualty care, Journal of Trauma and Acute Care Surgery, Aug. 1, 2021, 91 (2S Suppl 2): S40-S45, doi: 10.1097/TA.0000000000003263, PMID: 33938509.

Razzaghi, P., Tabrizian, A., Guo,W., Chen, S., Taye, A., Thompson, E., Bregeon, A., Baheri, A., Wei, P., A Survey on Reinforcement Learning in Aviation Applications, Nov. 3, 2022, available at: ArXiv. https://arxiv.org/abs/2211.02147, last accessed Jun. 25, 2024.

* cited by examiner

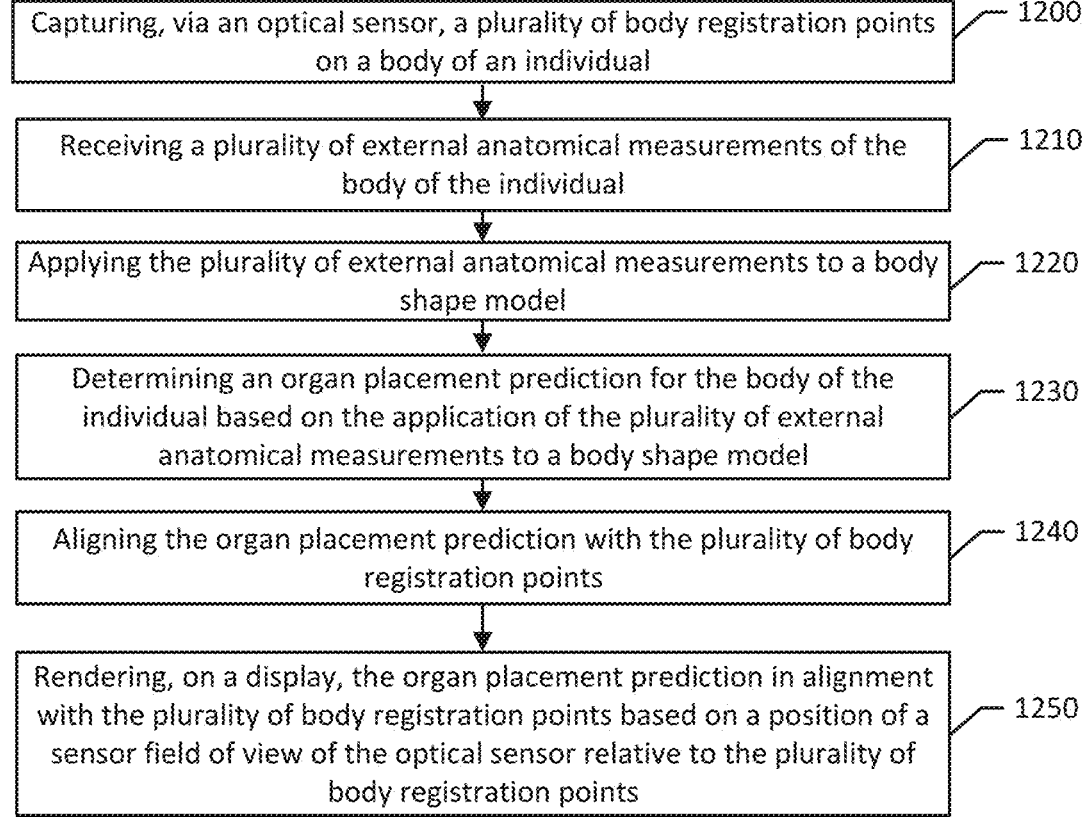

Capturing, via an optical sensor, a plurality of body registration points on a body of an individual ⟋— 1200

Receiving a plurality of external anatomical measurements of the body of the individual ⟋— 1210

Applying the plurality of external anatomical measurements to a body shape model ⟋— 1220

Determining an organ placement prediction for the body of the individual based on the application of the plurality of external anatomical measurements to a body shape model ⟋— 1230

Aligning the organ placement prediction with the plurality of body registration points ⟋— 1240

Rendering, on a display, the organ placement prediction in alignment with the plurality of body registration points based on a position of a sensor field of view of the optical sensor relative to the plurality of body registration points ⟋— 1250

FIG. 17

PREDICTIVE INTERNAL ANATOMY VISUALIZATION

CROSS-REFERENCE TO RELATED APPLICATIONS

This application claims the benefit of U.S. Provisional Application No. 63/499,167 filed on Apr. 28, 2023, the entire contents of which are hereby incorporated herein by reference.

TECHNICAL FIELD

Example embodiments generally relate to visualization technologies and, more particularly, relate to internal anatomy visualization.

BACKGROUND

The technology of internal anatomical imaging has substantially improved over the past few decades. X-ray computed tomography (CT) and magnetic resonance imaging (MRI) technology continue to evolve to provide more detailed information and images of the internal anatomy of patients in a non-invasive manner.

One drawback of such imaging techniques is that the equipment to perform such imaging is often large, has high power requirements, and must be operated in rather carefully controlled environments due to the radiation or magnetism. As such, x-ray and MRI machines are not generally useful for "in the field" care, i.e., care that is provided away from a healthcare facility. Such in the field care situations may be associated with car accidents, sports-related injuries, combat injuries, emergency calls involving paramedics, and the like.

To assist in delivering targeted medical care, particularly in the field, healthcare providers use various techniques to gain insights into the internal anatomy of a patient's body to identify, for example, the likely location of critical organs. In many instances, healthcare providers may rely on visual scans, touch and feel, and tacit knowledge to gain diagnostic information regarding the internal anatomy of a patient. Such information may prove useful when treating a patient that may be suffering from, for example, a trauma that may be causing internal bleeding, a cardiac event, heat exhaustion, or the like. Moreover, such external visual techniques may be used, not only for diagnostics, but also when delivering treatment to the interior of the patient's body (e.g., into the chest cavity), which may require, for example, vascular needle insertion, chest tube insertion, fluid delivery, or the like.

Unfortunately, the internal anatomical information obtained from conventional exterior visual scans, touch and feel, and tacit knowledge can often be inaccurate. The tacit knowledge that is often relied upon most heavily, particularly when time-sensitive care is needed, can be over-generalized across the population of patients. While such over-generalized information may be the best option for delivering time-sensitive care in the field, the resulting decisions regarding the internal anatomy of a patient can be inaccurate. As a result, the reliance on such an approach can include a risk that an inaccurate presumed internal anatomy can lead to unintended interaction with, for example, critical organs, when providing care that involves entry into the patient's body (i.e., chest tube insertion).

BRIEF SUMMARY OF SOME EXAMPLES

According to some example embodiments, an example anatomy visualization device is provided. The anatomy visualization device may comprise a display, and optical sensor, and processing circuitry. The optical sensor may be coupled to the display such that the optical sensor and the display maintain a known relative position to support presentation of augmented reality on the display. The optical sensor may have a sensor field of view. The processing circuitry may be configured to capture, via the optical sensor, a plurality of body registration points on a body of an individual, receive a plurality of external anatomical measurements of the body, apply the plurality of external anatomical measurements to a body shape model, and determine an organ placement prediction for the body of the individual based on the application of the plurality of external anatomical measurements to the body shape model. In this regard, the organ placement prediction may comprise organ position information, organ size information, and organ shape information for a plurality of organs. The processing circuitry may be further configured to align the organ placement prediction with the plurality of body registration points, and render, on the display, the organ placement prediction in alignment with the plurality of body registration points based on a position of the sensor field of view relative to the plurality of registration points. The organ placement prediction may be rendered as an augmented reality object that overlays a user's real-world view of the body of the individual or is integrated with an image of the body of the individual provided on the display.

According to some example embodiments, an example method for internal anatomy visualization in augmented reality is provided. The example method may comprise capturing, via an optical sensor, a plurality of body registration points on a body of an individual, receiving, by processing circuitry, a plurality of external anatomical measurements of the body, and applying the plurality of external anatomical measurements to a body shape model. The example method may also comprise determining an organ placement prediction for the body of the individual based on the application of the plurality of external anatomical measurements to the body shape model. The organ placement prediction may comprise organ position information, organ size information, and organ shape information for a plurality of organs. The example method may also comprise aligning the organ placement prediction with the plurality of body registration points, and rendering, on a display, the organ placement prediction in alignment with the plurality of body registration points based on a position of a sensor field of view of the optical sensor relative to the plurality of registration points. The organ placement prediction may be rendered as an augmented reality object that overlays a user's real-world view of the body of the individual or is integrated with an image of the body of the individual provided on the display.

According to some example embodiments, an example headset device is provided. The example headset comprises a support element configured to be worn on a head of a user, a display coupled to the support element and positioned to provide visual information to the user within a field of view of the user, and an optical sensor coupled to the support element such that the optical sensor and the display maintain a known relative position. The optical sensor may have a sensor field of view that at least partially overlaps the field of view of the user beyond the display. The example headset may also comprise processing circuitry configured to capture, via the optical sensor, a plurality of body registration points on a body of an individual, receive a plurality of external anatomical measurements of the body, apply the plurality of external anatomical measurements to a body shape model, and determine an organ placement prediction for the body of the individual based on the application of the plurality of external anatomical measurements to the body shape model. The organ placement prediction may comprise organ position information, organ size information, and organ shape information for a plurality of organs. The processing circuitry may be further configured to align the organ placement prediction with the plurality of body registration points, and render, on the display, the organ placement prediction in alignment with the plurality of body registration points based on a position of the sensor field of view relative to the plurality of registration points. The organ placement prediction may be rendered as an augmented reality object that overlays a user's real-world view of the body of the individual or is integrated with an image of the body of the individual provided on the display.

BRIEF DESCRIPTION OF THE SEVERAL
VIEWS OF THE DRAWING(S)

Having thus described embodiments of the invention in general terms, reference will now be made to the accompanying drawings, which are not necessarily drawn to scale, and wherein:

FIG. 17 illustrates a flowchart of an example method for implementing internal anatomy visualization in augmented reality according to some example embodiments.

DETAILED DESCRIPTION

Figure 1:
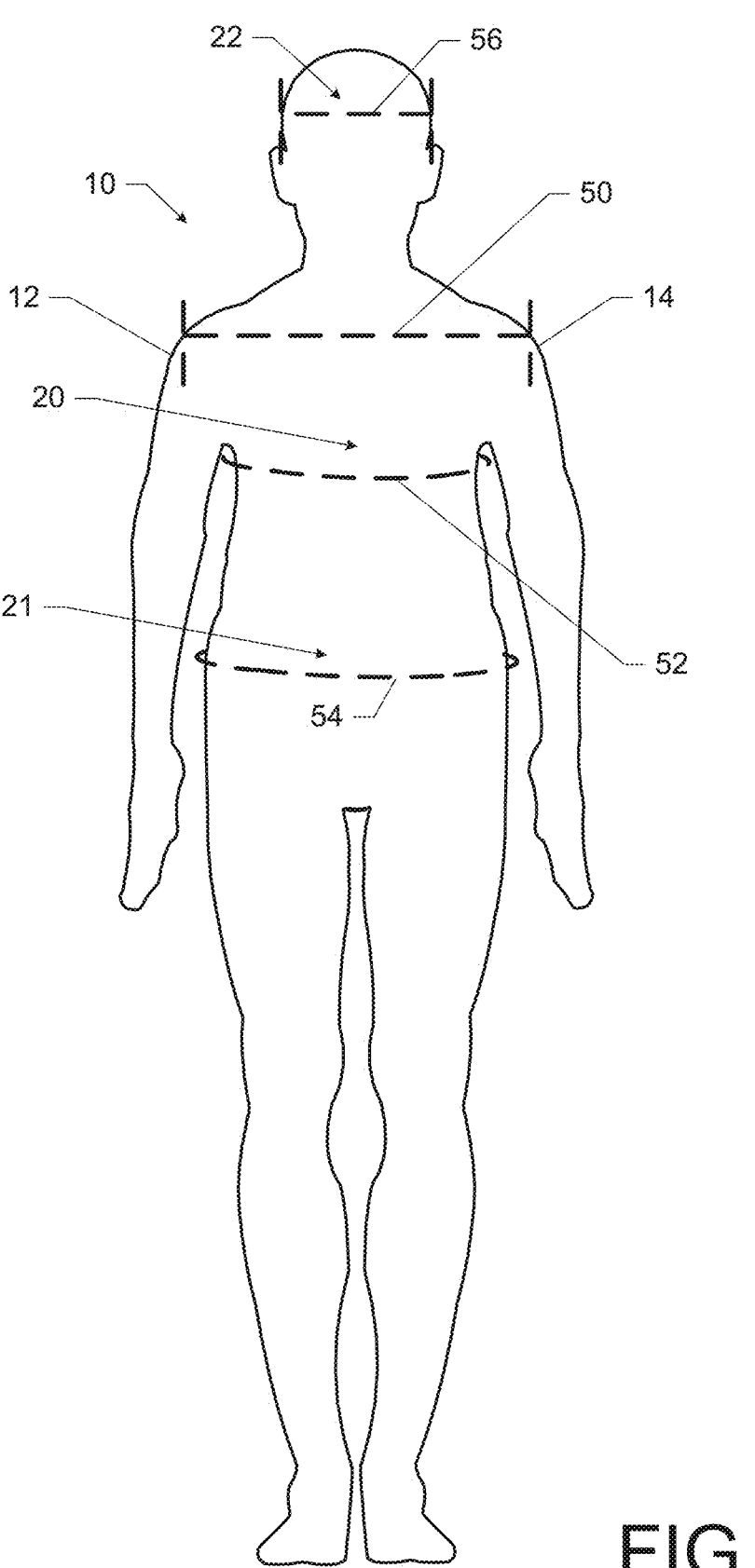
FIG. 1 illustrates an example body of an individual with indications of external anatomical measurements for use with a body shape model according to some example embodiments.

Some example embodiments now will be described more fully hereinafter with reference to the accompanying drawings, in which some, but not all example embodiments are shown. Indeed, the examples described and pictured herein should not be construed as being limiting as to the scope, applicability, or configuration of the present disclosure. Rather, these example embodiments are provided so that this disclosure will satisfy applicable legal requirements. Like reference numerals refer to like elements throughout.

According to various example embodiments, a predictive internal anatomy visualization solution is provided that enables, for example, a healthcare provider to visualize an individual's (e.g., patient's) internal organs in real time, in a remote location, based on external measurements of the patient. Such a solution can have widespread applicability to enable healthcare personnel to, in at least some instances, administer life-saving procedures due to the ability to visualize the position, size, and shape of an individual's internal organs while performing such procedures, without the need for x-ray machines, MRI machines, or exploratory surgery. As such, targeted care, for example, into an individual's chest cavity can be performed in a visual manner by permitting the healthcare provider to "see" into the chest cavity of the individual via augmented reality that generates an informative presentation of the individual's internal organs to form an intuitive healthcare interface.

According to some example embodiments, a predictive internal anatomy visualization system or device is provided. Such a system or device may leverage a pre-generated body shape model that can be used to predict the locations, sizes, and shapes of organs internal to the human body based on anatomical measurements of an individual's body. Such organs, which, as used herein, may reference internal organs, such as the lungs, heart, stomach, kidneys, or the like, as well as, vascular structures such as arteries and veins, respiratory structures such as the trachea and bronchial tubes, digestive structures such as bladders and intestines, skeletal structures such as the spine and rib cage, and the like. According to some example embodiments, the anatomical measurements may be external anatomical measurements of the individual's body, such as a shoulder-to-shoulder distance, a perimeter length around the individual's chest (e.g., at the armpits or across the nipples), or the like.

The external measurements, in some example embodiments, may be taken in real-time (i.e., immediately before care is to be provided) or at an earlier time to permit the measurements to be stored for use once an identity of the individual is known. Based on the external anatomical measurements, and possibly other inputs, the body shape model may output an organ placement prediction that includes information regarding the position, size, and shape of organs for an individual with those external anatomical measurements. After a registration process that involves identifying body registration points on the individual's body, a registered rendering of internal organs based on the organ placement prediction may be displayed, for example, on a headset worn by a healthcare provider. The registered rendering may be provided in augmented reality, such that the internal organs appear, in appropriate locations based on the registration, together with the body of the individual so that healthcare procedures may be performed by the healthcare provider while have an integrated visualization of the individual's actual body, together with the registered rendering of the internal organs. As such, the healthcare provider may be enabled to perform procedures with information to avoid or interact with internal organs within the body of the individual.

The body shape model that may be used to provide the organ placement prediction, according to some example embodiments, may be a statistically-constructed model developed using, for example, machine learning to specifically define a relationship between the external anatomical measurements of individuals and the position, size, and shape of the internal organs of individuals. In this regard, a model training process for the body shape model may include, for a minimum number of individuals, capturing external anatomical measurements of an individual and performing an x-ray, MRI, or other internal imaging of the individual that captures position, size, and shape information for structures within the same individual. The model training process may then employ machine learning to develop an associative algorithm that describes a relationship between external anatomical measurements and the position, size, and shape of organs. The model training process may also perform machine learning based on, in addition to external anatomical measurements, other externally determinable human characteristics, such as height, weight, and demographic characteristics, to further refine the body shape model. According to some example embodiments, an external shape estimation may also be a factor that may integrated into the body shape model. The demographic characteristics may include gender, age, ethnicity, or the like. Each of the demographic characteristics may be factored into and added to the machine learning to build multi-dimensional relationships between the external anatomical measurements, the demographic characteristics, and the position, size, and shape of internal organs. Accordingly, with the addition of further individuals to the model training process, an increasingly refined body shape model may be developed. However, according to some example embodiments, in instances where an individual's information (i.e., the individual's external anatomical measurements, demographic characteristics, and position, size, and shape of internal structures) does not contribute to convergence of the body shape model within a defined convergence threshold, the machine learning process may determine that the individual's information is an anomaly, and the individual's information may be disregarded from consideration for further refining the body shape model.

According to one example embodiment, a body shape model may be generated based on CT imaging of a population of at least one hundred and fifty (e.g., one hundred and eighty) people as the sample set. To ensure sufficient diversity of information from the sample set, minimum threshold percentages of characteristics may be required for the sample set. For example, the sample set may include fifty percent female and fifty percent male. Similarly, diverse ethnicity and age thresholds may also be required, for example, with the percentages being aligned with the population of a country, a state, an organization, or the like. Additionally, a required distribution of weights, heights, physique, skeletal proportions, and the like may also be included in the sample set.

As mentioned above, X-ray CT or MRI images of each individual of the sample set may be captured and the data of the captures may be provided to a machine learning algorithm (e.g., a segmentation algorithm) for processing. According to some example embodiments, the CT images from each individual may comprise over one hundred planar image slices of the individual's body. The machine learning algorithm may be configured to compile the planar image slices and extract internal anatomical structures, for example, sixty-six anatomical structures per person. According to some example embodiments, the shape variation of each organ may be described by mathematical methods, such as, for example, principal component analysis or latent space encoding. According to some example embodiments, the machine learning processing may be performed with respect to external anatomical measurements and demographic characteristics that have been predefined due their ability to be readily determined in the field or via feature extraction processing from in the field image captures. According to some example embodiments, a variety of the external anatomical measurements and demographic characteristics for use as convergence parameters to generate the body shape model as a relational model with organ position, size, and shape. Example external anatomical measurements for use in the machine learning may include shoulder-to-shoulder distance, chest circumference, waist circumference, temple-to-temple distance, height, arm length, leg length, or the like. Weight may be another parameter that may be used. According to some example embodiments, the demographic characteristics that may be included for machine learning may include age, gender, ethnicity, and the like. The machine learning used to develop the body shape model may be based on a number of different machine learning algorithms that use relational data analysis to generate a model that describes the input dataset.

In this regard, for example, a tree-based or neural network machine learning approach may be used. More specifically, according to some example embodiments, various algorithms may be used, such as, for example, regression algorithms (e.g., ordinary least squares regression (OLSR), linear regression, logistic regression or the like), instance-based machine learning algorithms (e.g., k-nearest neighbor (kNN) or the like), regularization algorithms (e.g., ridge regression and the like), decision tree algorithms (e.g., Chi-squared automatic interaction detection (CHAID) and the like), Bayesian algorithms (e.g., Bayesian network (BN) and the like), clustering algorithms (e.g., k-Means and like), association rule learning algorithms (e.g., apriori or the like), artificial neural network algorithms (e.g., multilayer perceptrons (MLP) or the like), deep learning algorithms (e.g., convolutional neural network (CNN) or the like), dimensionality reduction algorithms (uniform manifold approximation and projection for dimension reduction (UMAP) or the like), ensemble algorithms (e.g., bootstrapped aggregation (Bagging) or the like), or the like.

Once the body shape model is generated, according to some example embodiments, the body shape model may be maintained and improved via the addition of data for processing into the model. In this regard, regardless of diversity of data, internal imaging information (via X-ray CT, MRI, or the like) may be added to the model to either increase the certainty weightings or introduce new model components due to minimal or no previous data that determined a meaningful relationship for inclusion in the model. According to some example embodiments, as mentioned herein, data that fails to converge within a threshold relationship space may be quarantined from inclusion in the body shape model for either being anomalous or for introducing increased uncertainty after a strong relationship has been identified. In this manner, the body shape model may remain relatively streamlined, concise, and efficient, which may be of particular value in remote contexts with no communications connectivity, thereby requiring that the body shape model be stored locally on a predictive internal anatomy visualization device.

According to some example embodiments, the input data (e.g., the external anatomical measurements, the demographic characteristics, and the like) may be processed into a data structure for application to the body shape model. Application of this input data structure to the body shape model may comprise a multi-dimensional comparison of dimension of the input data structure to the various dimensions (e.g., external anatomical measurements, demographic characteristics, and the like) that define the body shape model. According to some example embodiments, a confidence matrix may be generated that describes the relational confidence of each dimension with the dimensions of the body shape model. In this regard, the dimensional comparisons may be optimized, for example, through an iterative process, to determine a highest confidence match in the multi-dimensional space defined by the dimensions of the body shape model. According to some example embodiments, a confidence score may be determined based on the confidence matrix, and the confidence score may describe a degree of confidence or fit of the input data structure to the highest confidence match with the body shape model. According to some example embodiments, if the confidence score is higher than a threshold confidence level, then an organ placement prediction that is linked to the highest confidence match may be provided as an output from the input data being applied to the body shape model. If the confidence score is lower than the threshold confidence level, then no result is determined and no organ placement prediction is provided.

In some example embodiments, the external anatomical measurements and demographic characteristics for a given individual may already be stored and therefore the external anatomical measurements and the demographic characteristics may be known to the predictive internal anatomy visualization device, prior to encountering the given individual. To retrieve the stored external anatomical measurements and demographic characteristics to be input into the body shape model, an identity of the individual may first be determined and provided as an input to measurement dataset. According to some example embodiments, an individual may wear or include a unique identifier element on their clothing or body, which may be, for example, read by a sensor (e.g., optical sensor, barcode scanner, RFID reader, or the like). In this regard, the individual may have a tattoo, identification tags (e.g., dog tags), bracelet or clothing with, for example, a bar code (e.g., a QR code) or an RFID tag having a unique code assigned to the specific individual, which may be read by the sensor. A predictive internal anatomy visualization device may then use the received unique code to query a measurement dataset and retrieve the external anatomical measurements and demographic characteristics from the stored measurement dataset. Alternatively, in some example embodiments, biometric-based identification sensors or manual entry of a name or code for the individual may be used to determine the unique code to retrieve the external anatomical measurements and demographic characteristics for an individual.

According to some example embodiments, the determination of external anatomical measurements and demographic characteristics need not be previously stored, but may rather be measured or determined by the predictive internal anatomy visualization device. In some instances, the identity of an individual may not be known or may not be readily determined. As such, according to some example embodiments, external anatomical measurements and demographic characteristics may be captured directly via various sensors (e.g., optical sensors including, for example, a camera, a lidar sensor, a laser scanning sensor, or the like) directed at the individual. External anatomical measurements may be taken in a variety of manners and used as direct inputs to the body shape model. Similarly, according to some example embodiments, demographic characteristics may be determined, for example, visually and provided as inputs to the body shape model.

For example, according to some embodiments, a scan of the individual's body performed by a sensor may be sufficient for the captured images to be processed to determine the external anatomical measurements for use with the body shape model. Alternatively, according to some example embodiments, external anatomical measurements may be determined by employing a pointing implement within the field of view of a sensor to indicate measurement positions. Such measurement positions may be processed to determine lengths (e.g., a shoulder-to-shoulder distance) for use as an external anatomical measurement. According to some example embodiments, to indicate that the pointing implement is located at a desired measurement position, a user may actuate a switch (e.g., a button) on the pointing implement to indicate that a position capture of the pointing implement may be performed and evaluated. In this manner, various external anatomical measurements may be determined and used as inputs to the body shape model to generate an organ placement prediction. Additionally, demographic characteristics may be entered via a user interface (e.g., spoken in to a microphone, typed on a keypad, etc.) to be captured and evaluated in combination with the external anatomical measurements.

According to some example embodiments, to render the organ placement prediction in augmented reality, the coordinate information of the organ placement prediction may be registered to a body registration points on the individual's body. In this regard, according to some example embodiments, a plurality of body registration points may be defined, and a user point or mark those locations using, for example, the pointing implement. With the body registration points being defined, model registration points of the organ placement prediction may be used to render the organ placement prediction on the display in augmented reality and in proper alignment with the individual's body. According to some example embodiments, the body registration points may be processed to generate a registration frame that can be used with the model registration points to register the rendered organ placement prediction with the body of the individual.

According to some example embodiments, a predictive internal anatomy visualization device may comprise a wearable headset device having a wearable display over the user's eyes. Such a display may have some degree of transparency, such that the user can see through the display to the external environment, but rendered elements may still be provided on the display, for example, as foreground information. Alternatively, according to some example embodiments, the display may be opaque (not able to be seen through), however, via optical sensors, the external environment may be reproduced on the display with other information, such as an organ placement prediction. Additionally, the display of the wearable headset may have a spatial relationship with sensors of the predictive internal anatomy visualization device, such that movement of the user's head moves the display and the sensors in a predictable manner (e.g., in unison). The sensors may therefore have a field of view that is static relative to the user's optical field of view. Based on this relationship, a registered rendering of the organ placement prediction may be presented on the wearable display. Moreover, registration of the rendered organ placement prediction with the individual's body may be maintained, even with movement of the field of view of the sensors. Accordingly, the portion of the individual's body that is currently within the sensor's (and thus the user's) field of view may be shown with a portion of the organ placement prediction positioned accurately due to the registration of the organ placement prediction with the individual's body. Additionally, according to some example embodiments, a depth of view of the organ placement prediction may be selected, which may provide the user with a two-dimensional presentation of the body at a selected cross-sectional depth. In this manner, for example, organs that may be closer to the exterior may be removed from the visualization, thereby eliminating foreground organs and foreground clutter from the displayed presentation, which would otherwise inhibit a user's ability to perform a health-care operation due to, for example, an obstructed view. In this regard, according to some example embodiments, the user may alternatively select categories of organs, such as those of the respiratory system, the vascular system, the digestive system, or the like to be rendered, for example, in isolation in augmented reality on the display.

Having described various aspects of some example embodiments in a more general sense, reference to the figures will now be made to further describe various example embodiments. Now referring to FIG. 1, a body 10 of an individual is shown. As mentioned above, certain external anatomical measurements of the body 10 may be used to determine a predicted position, size, and shape of organs within the body 10. In this regard, according to some example embodiments, one example external anatomical measurement that may at least partially correlate (i.e., with other measurements) with the position, size, and shape of organs may be the shoulder-to-shoulder distance 50. The shoulder-to-shoulder distance 50 may be defined as the distance between a point 14 on the dermal surface closest to the acromion bone of the left shoulder and a point 12 on the dermal surface closest to the acromion bone of the right shoulder. The shoulder-to-shoulder distance 50 may be one of a plurality of external anatomical measurements that may be considered to develop a correlated relationship to the position, size, and shape of organs within the body.

According to some example embodiments, another example external anatomical measurement that may at least partially correlate with the position, size, and shape of organs may be a circumference 52 of an individual's chest 20. The circumference 52 (or perimeter) of an individual's chest 20 may be defined as a distance around the user's body at the armpits (under the arms). Another measure of the circumference 52 may be defined across the nipples. The chest circumference 52 may be one of a plurality of external anatomical measurements that may be considered to develop a correlated relationship to the position, size, and shape of organs within the body 10.

According to some example embodiments, another example external anatomical measurement that may at least partially correlate with the position, size, and shape of organs may be a circumference 54 of at an individual's waist 21. The circumference 54 (or perimeter) of an individual's waist may be defined as a distance around the user's body at the peaks of the pelvic bones (i.e., the peaks of the ilium). The waist circumference 54 may be one of a plurality of external anatomical measurements that may be considered to develop a correlated relationship to the position, size, and shape of organs within the body 10.

Further, according to some example embodiments, another example external anatomical measurement that may at least partially correlate with the position, size, and shape of organs one example external anatomical measurement that may at least partially correlate (i.e., with other measurements) with the position, size, and shape of organs may be the temple-to-temple distance 56. The temple-to-temple distance 56 may be defined as the distance on the head 22 between a point on the dermal surface of the right temple and a point on the dermal surface of the left temple. The temple-to-temple distance 56 may be one of a plurality of external anatomical measurements that may be considered to develop a correlated relationship to the position, size, and shape of organs within the body 10.

Figure 2:
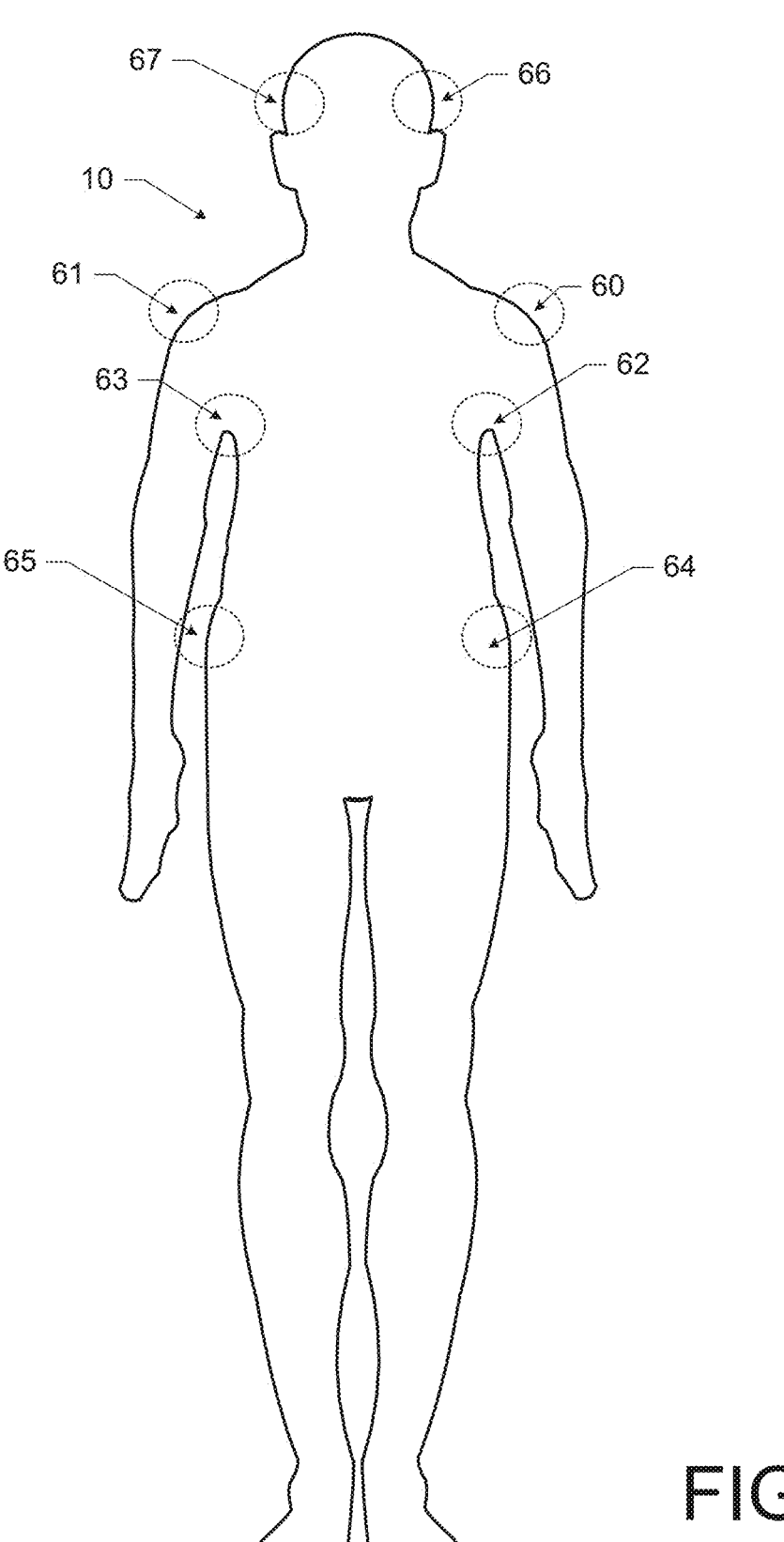
FIG. 2 illustrates an example body of an individual with indications of measurement locations or registration location points according to some example embodiments.

Having defined various external anatomical measurements that may be used for predicting the position, size, and shape of organs, reference is now made to FIG. 2, which indicates measurement locations that may be used to determine corresponding external anatomical measurements. If the relative location of the measurement locations for a corresponding external anatomical measurement is known, then the external anatomical measurements on the body 10 may be determined. For example, if location 60, being a point on the dermal surface closest to the acromion bone of the left shoulder, and location 61, being a point on the dermal surface closest to the acromion bone of the right shoulder, are determined, then the shoulder-to-shoulder distance 50 may be determined. In this regard, according to some example embodiments, a spatial processing technique may be used to process captured images to determine spatial relationships with the images that may be used to measure actual distances, such as the distance between location 60 and 61 to determine the shoulder-to-shoulder distance 50. The temple-to-temple distance 56 may be measured in a similar manner by determining the location 66, being the left temple, and the location 67, being the right temple.

Additionally, if the location 62, associated with the left armpit, and the location 63 associated with the right armpit, are determined, then the chest circumference 52 may be determined. In this regard, for example, a distance from the location 62 to the location 63 may be determined via spatial processing of captured images, and that distance may be, for example, doubled to determine the chest circumference 52. The waist circumference 54 may be measured in a similar manner by determining the location 64, being the left pelvic bone peak, and the location 65, being the right pelvic bone peak.

As further described herein, the locations 60, 61, 62, 63, 64, 65, 66, and 67 may used, not only for external measurements, but also for registration. In this regard, these locations on the body 10 (or others) may be used to determine a configuration of the body 10 as reference point locations. Such reference point locations may therefore be used for alignment with an organ placement prediction as further described herein.

Figure 3:
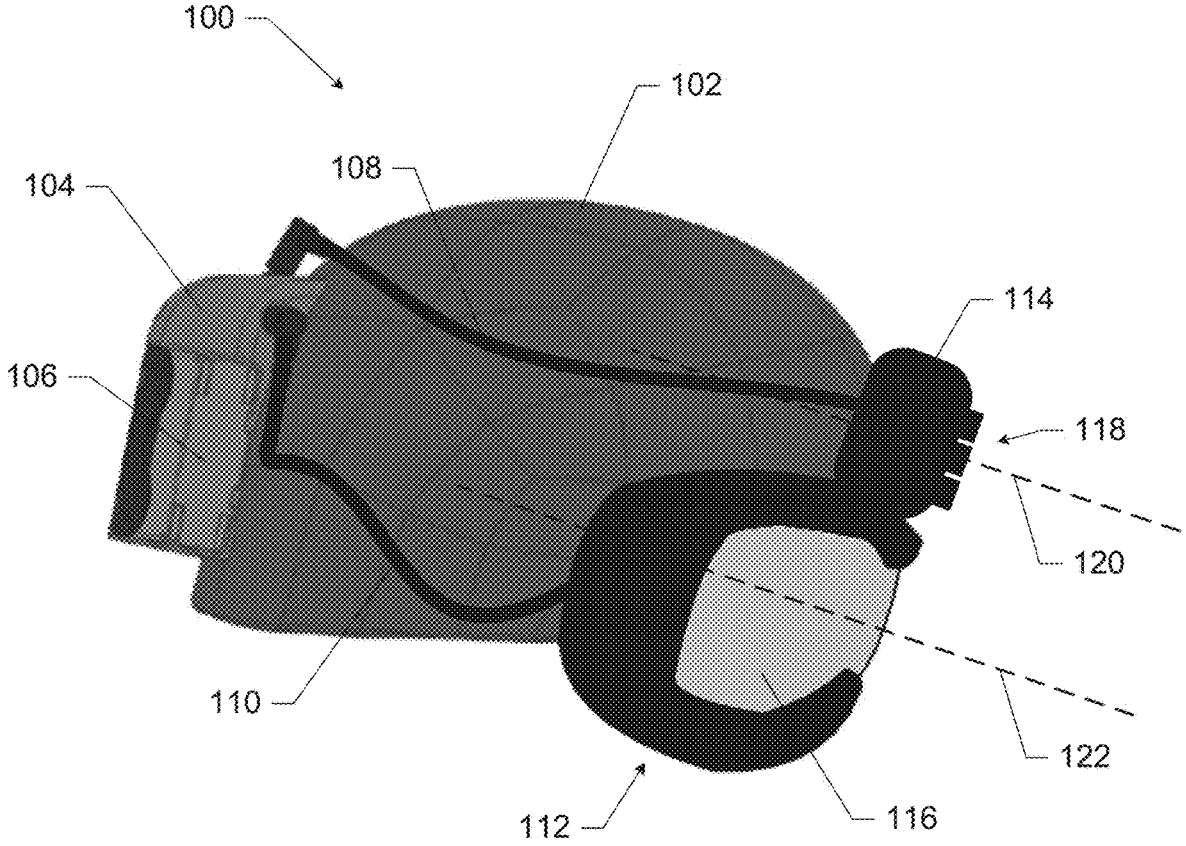
FIG. 3 illustrates a predictive internal anatomy visualization device in the form of a headset according to some example embodiments.

Reference is now made to FIG. 3, which illustrates an example predictive internal anatomy visualization device in the form of a wearable headset 100. The headset 100 may comprise a helmet 102, a processing circuitry housing 104, and a battery 106. The helmet 102 may be an example of a support element that is configured to be worn on a head of a user and support various components of the headset 100, including, for example, the processing circuitry housing 104 and the battery 106. Additionally, according to some example embodiments, the headset 100 may include an optical assembly 112, which may comprise an over-eye display 116 and a sensor assembly 114 comprising a plurality of sensors 118. According to some example embodiments, power and data connections between the display 116 and the processing circuitry housing 104 may made via cabling 110. Further, according to some example embodiments, power and data connections between the sensor assembly 114 and the processing circuitry housing 104 may made via cabling 108.

As an example of a predictive internal anatomy visualization device according to some example embodiments, the headset 100 may be configured to obtain external anatomical measurements, generate an organ placement prediction, and render the organ placement prediction in augmented reality on the over-eye display 116 in registration with the body of an individual. In this regard, the sensor assembly 114 may include various sensors 118, including optical sensors. Such optical sensors may be embodied as, for example, cameras, lidar sensors, laser scanning sensors, or the like. An optical sensor of the sensors 118 may be configured to capture images (or scans) of the field of view of the optical sensor. The captured images may, for example, be within the visible spectrum. However, according to some example embodiments, sensors may be included that capture images of the body of the individual at other, non-visible wavelengths, such as for example, infrared, ultraviolet, or radio wavelengths, or the like. According to some example embodiments, the sensors may include a thermal imaging sensor that captures images that depict temperatures using colors in the image.

The sensors 118 may include or be operatively coupled to spatial sensors (e.g., time-of-flight, active infrared illumination, lidar sensors, laser scanning sensors, or the like). Such spatial sensors may measure spatial information, such as the location, field of view direction, and orientation, of the sensors 118 and the headset 100. Such spatial information may be combined, based on timing, with and image captured by the optical sensor to provide a spatial context for the image. The processing circuitry of the headset 100 (e.g., processing circuitry 1010 of FIG. 15) may be configured to leverage the spatial context of the captured images to integrate augmented reality elements into a visualization of, for example, an individual's body as described herein. For example embodiments that include a transparent display 116, a spatial relationship between the field of view of the user through the display 116 and a field of view of the sensors 118 may be defined and static. In this regard, according to some example embodiments, a field of view centerline 120 of the sensors 118 may be maintained parallel with a field of view centerline 122 of the user's eyes through the display 116. This known relative relationship between the position of the field of view of sensors 118 and the position of the field of view of the user's eyes may be accounted for when rendering elements in augmented reality to ensure proper registration.

As mentioned above, the headset 100 may include an over-eye display 116. The display 116 may be controlled and driven by processing circuity, for example, located in the processing circuitry housing 104. Such processing circuitry, the display 116, and the sensor assembly 114 may be powered by the battery 106, which may be removable and/or rechargeable. Moreover, the over-eye display 116 may be a transparent display or an opaque display. In this regard, as a transparent display, a user may be able to see through the display and directly see objects in the real world. Renderings on the transparent display may appear as rendered elements that overlay the real world objects. In this regard, with a transparent display, an organ placement prediction may be rendered as a registered overlay of organs on the directly viewed real world body of the individual. Alternatively, as an opaque display, the user may not directly see the real world, and the display may render both the real world elements and the augmented reality elements as an integrated visualization. In this regard, an optical sensor may capture images of the field of view of the of the optical sensor, and such images may be combined with a registered rendering of, for example, an organ placement prediction to provide the user with a visualization of an individual's body with its internal organs.

The headset 100 provides an example embodiment of a predictive internal anatomy visualization device or system according to some example embodiments. However, it is understood that a predictive internal anatomy visualization device may be implemented in a variety of form factors, for example, depending upon the use case for the organ placement prediction. In this regard, rather than being a headset or other mobile implementation, the predictive internal anatomy visualization device may be stationary for use, for example, in a healthcare facility or clinic. In this regard, rather than an over-eye display, the display 116 may be, for example, a monitor coupled to a movable arm with associated sensors, and the monitor may be positioned over an individual's body to render the organ placement prediction with the user's body for viewing by a doctor or surgeon that uses the augmented reality visualization while performing healthcare procedures.

As mentioned above, rendering the organ placement prediction in an augmented reality visualization may require registration of the organ placement prediction with the body of the individual. To maintain registration between the individual's body and the organ placement prediction, a plurality of body registration points may be defined. In this regard, each registration point location may correspond to a predetermined location on the body. For example, with reference again to FIG. 2, location 60 may correspond to the position of the left shoulder. As such, when defining the body registration points, the processing circuitry of the headset 100 may request that the user locate and cause the device to capture a position of the left shoulder. As such, the user may, for example, move a pointing implement to location 60 and trigger the processing circuitry to perform a capture of the position of the pointing implement. In response, the processing circuitry may define the spatial position of the left shoulder for use as a registration point location. Additional body registration points may be captured and defined in a similar manner, until a sufficient number of body registration points are defined to support registration of the organ placement prediction.

According to some example embodiments, rather than capturing and defining individual body registration points, the processing circuitry of the headset 100 may be configured to automatically define body registration points. In this regard, the processing circuitry may be configured to enter a registration mode and request that the user visually scan the individual to capture a plurality of images of the body of the individual for spatial analysis. In this regard, the processing circuitry may be configured to evaluate the images and their associated spatial relationships to identify body features, such as, for example, armpits, using an external body model. According to some example embodiments, such an evaluation of images may account for clothing (e.g., loose fitted clothing). However, in instances where the individual wears a uniform (e.g., military personnel), clothing may be more readily accounted for, since the style and fit of the clothing may be more predictable. Further, according to some example embodiments, an example uniform may include reference point indications (e.g., markings) on the clothing itself at desired locations and possibly with positional codes within the indications. Such markings may be either visible or non-visible (e.g., reflecting or emitting radiation outside of the visible spectrum). In such example embodiments, reference point locations may be defined by identifying the reference point indications on the clothing via spatial analysis of the captured images that include such indications.

Figure 4:
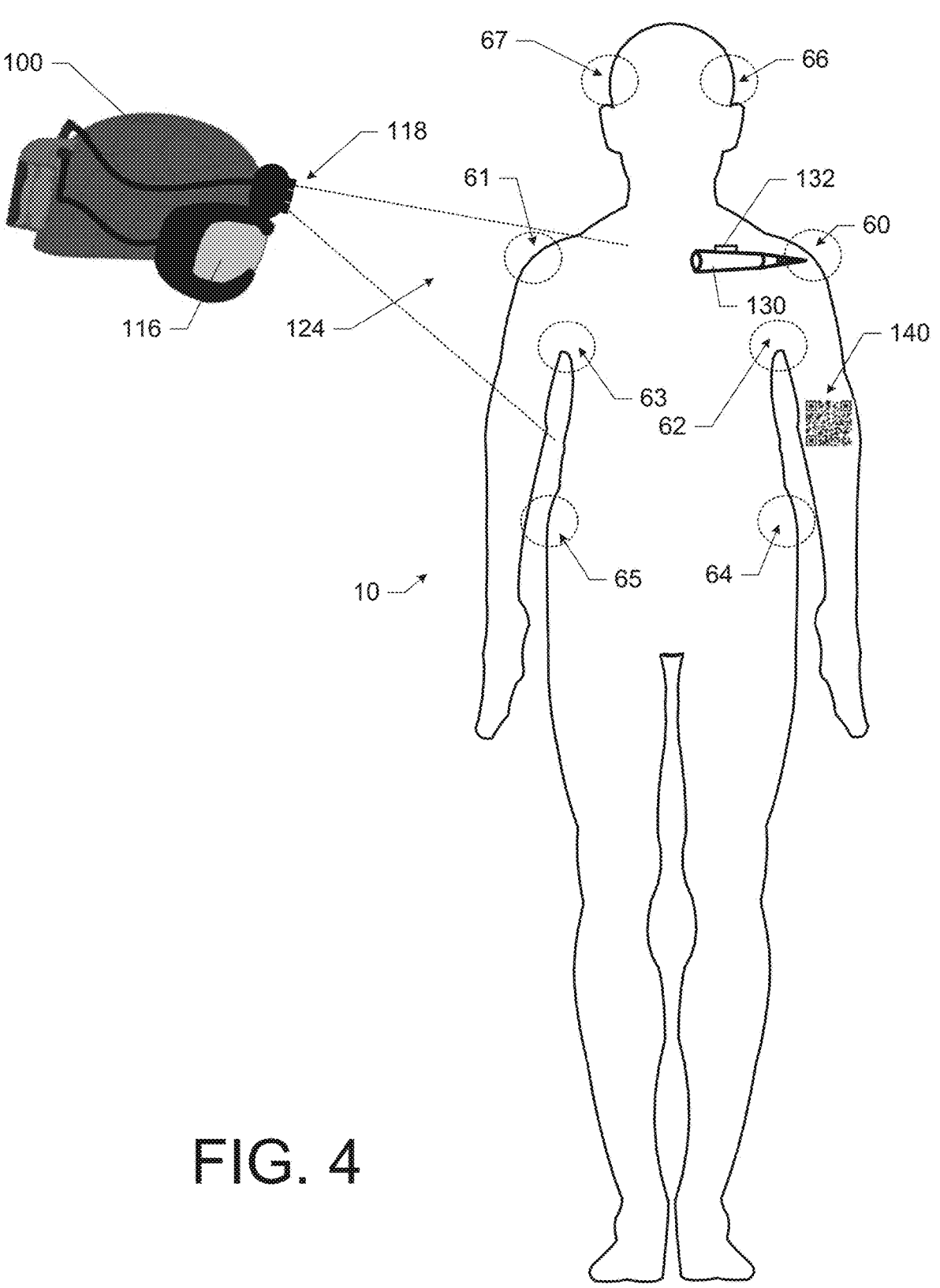
FIG. 4 illustrates a pointing implement capture of a measurement location or a registration point location within the field of view of the sensors of the headset according to some example embodiments.

FIG. 4 provides a more detailed illustration of location capturing using a pointing implement 130 to either obtain external anatomical measurements or define body registration points. In either case, a user may be wearing the headset 100 while performing such operations. As can be seen in FIG. 4, the sensors 118 have a field of view 124. According to some example embodiments, the pointing implement 130 may be used to point to a location for capture as location for external anatomical measurements, as a location for a registration point location, or for both.

In this regard, an example scenario for measuring a shoulder-to-shoulder distance 50 is described. To start the external anatomical measurement process, the user may, for example, make a selection via a user interface of the headset 100 (e.g., via a microphone using voice commands, pressing a button, using a keypad, etc.) to begin a shoulder-to-shoulder distance measurement. The processing circuitry of the headset 100 may prompt the user, for example, via verbal instructions provided through a speaker (or through the display 116), to move the pointing implement 130 to the left shoulder of the individual and trigger a location capture. Since the user is viewing the body 10 using the display 116, the pointing implement 130 should be in the field of view of the user and thus the field of view 124 of the sensors 118 to capture the position of the pointing implement 130. As such, in response to the prompt, the user may move the pointing implement 130 to the location 60 that is associated with the individual's left shoulder and trigger a location capture. To trigger the location capture, the user may actuate a capture switch 132, for example, disposed on the pointing implement 130. Alternatively, according to some example embodiments, the user may use voice commands to request a location capture once the pointing implement 130 is in position. The pointing implement 130, according to some example embodiments, may have a distinguishable tip (e.g., with a pattern, a light, or the like) that may be readily identified via image processing by the processing circuitry. According to some example embodiments, the tip of the pointing implement 130 may include a light source, similar to a laser pointer, to indicate the desired location on the body 10 for capture as a desired location. In response to triggering the location capture, the processing circuitry may be configured to evaluate the captured images of the body 10, in association with the spatial information to define the left shoulder location. A similar procedure may be performed for the right shoulder to define the right shoulder location at location 61. Once the right and left shoulder locations are defined, the processing circuitry may spatially analyze these locations to determine a distance between the locations, and thus the shoulder-to-shoulder distance 50.

As mentioned above, external anatomical measurements may be determined in a similar manner via capture locations of the pointing implement 130, for example, in response to respective prompts for desired locations. Moreover, a similar procedure may be performed to define body registration points for use in registration of an organ placement prediction. Additionally, other information about the individual may be input via, for example, a user interface of the headset 100. In this regard, demographic characteristics may be input, such as gender, age, and ethnicity. In some example embodiments, an estimate or measurement of individual's weight and height may also be provided as inputs.

According to some example embodiments, an individual may wear or include a unique identifier element on their clothing or body, which may be used to retrieve pre-stored external anatomical measurements and demographic characteristics of the individual. In this regard, where, for example, the individual is in a closed, known group, such as on a work site, an employee, the military, or the like, the individual may be required to have an identification element on their person at all times. For example, the individual may be required to have a badge, bracelet, clothing, or the like that may, for example, be read by a sensor 118 of the headset 100. In this regard, such identification element may be a bar code (e.g., a QR code) or an RFID tag having a unique code assigned to the specific individual, which may be read by a sensor 118. As such, according to some example embodiments, the sensors 118 may include an RFID reader.

In the example embodiments shown in FIG. 4, a QR code 140 is included, for example, on clothing on the body 10. Accordingly, an optical sensor of the headset 100 may be configured to capture an image of the QR code 140, and the processing circuitry of the headset 100 may be configured to interpret the QR code in the captured image to determine a unique code for the individual. As described herein, the unique code may be used to rapidly query a measurement dataset to retrieve the specific external anatomical measurements and demographic characteristics of the individual to be applied to the body shape model and determine an organ placement prediction.

According to some example embodiments, biometric-based identification technologies may be used to determine an identification of an individual and retrieve, for example, external anatomical measurements and demographic characteristics for the individual. In this regard, the processing circuitry of the headset 100 may be configured to perform facial recognition to identify the individual. Alternatively, the sensors 118 may include a retinal scanner that may be used to identify the individual. Alternatively, the headset 100 may include a fingerprint scanner that may be used to identify the individual.

Additionally, as mentioned above, a three-dimensional (3D) scan of the exterior of an individual may be captured, and image processing may be performed to determine external anatomical measurements. According to some example embodiments, the 3D scan may be performed in the field upon arriving at the individual that is in need of healthcare services as part of a diagnostic process. Such a 3D scan may performed using a depth camera or laser scanning sensor that uses signal response timing to generate a 3D map of an object, in this case, the exterior of the body of an individual. The processing circuitry may perform, for example, feature extraction based on a measurement dataset (e.g., measurement model) to identify features of the 3D map that can be correlated to, for example, the individual's head, feet, armpits, shoulders, hands, and the like. The relative spatial position of the extracted features may also be determined by the processing circuitry, and, in turn, distances between the extracted features may be determined or converted into, for example, external anatomical measurements for use with the body shape model.

Figure 5:
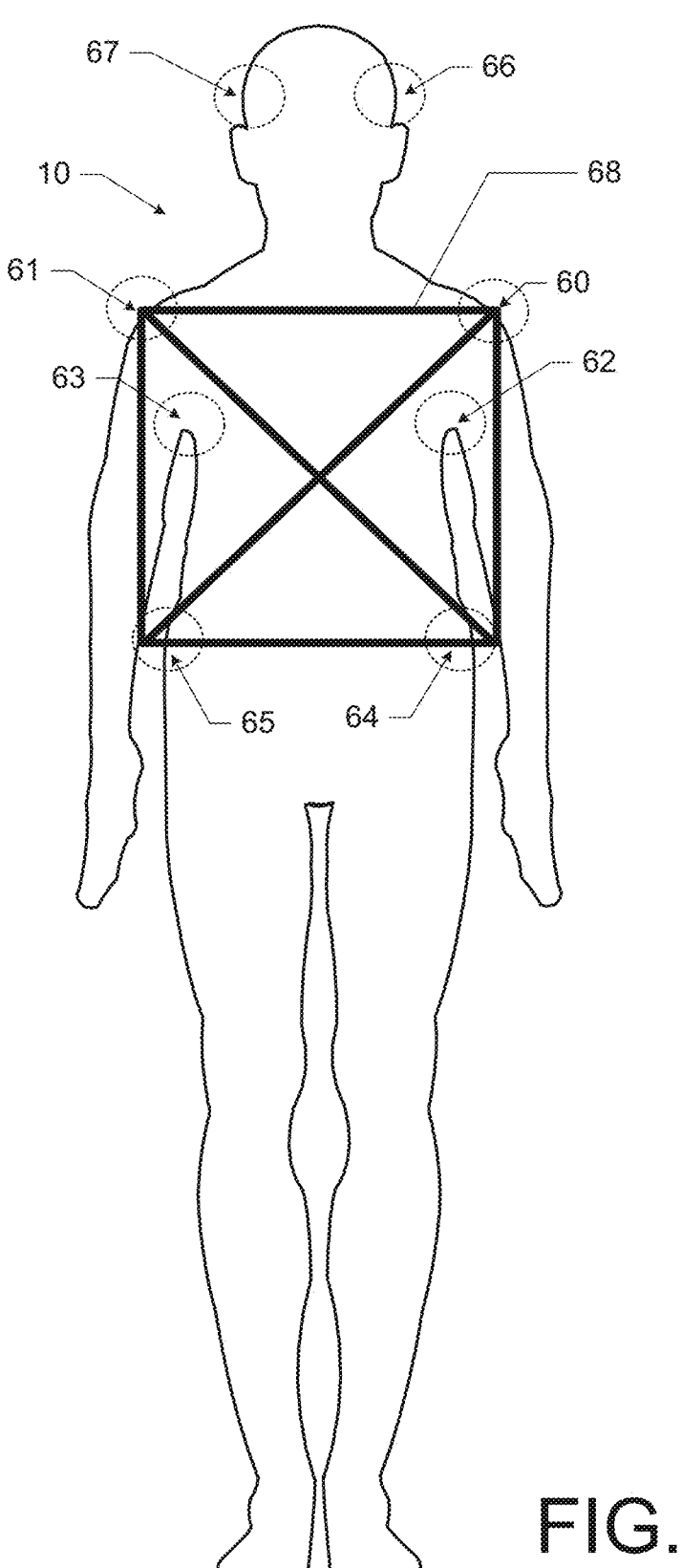
FIG. 5 illustrates an example body of an individual with a defined registration frame disposed on the body of an individual for use in a registration process according to some example embodiments.

Now referencing FIG. 5, the body 10 is shown in association with a reference frame 68. In this regard, according to some example embodiments, the processing circuitry of the headset 100 may be configured to convert a plurality of body registration points into a shape-based element for use in a registration process with an organ placement prediction. In this regard, for example, the registration frame 68 may be used to simplify the processing associated with registration maintenance when a user of the headset 100 is changing the field of view. The example registration frame 68 may be defined by a rectangle with corner diagonals that intersect at a center of the rectangle. The registration frame 68 may be positioned such that a top right corner is positioned on the left shoulder (i.e., location 60) and the top left corner is positioned on the right shoulder (i.e., location 61). Additionally, according to some example embodiments, the bottom side of the registration frame 68 may intersect with the left and right peaks of the pelvic bones (i.e., the peaks of the ilium) at locations 64 and 65 respectively. According to some example embodiments, the processing circuitry of the headset 100 may be configured to optimize registration maintenance by determining streamlined spatial processing using the registration frame 68, as opposed to individual points that may require relatively more processing to implement.

Regardless of whether a body registration points or a registration frame is used to determine a spatial definition of the body 10, the organ placement prediction may be registered to this spatial definition. In this regard, according to some example embodiments, an organ placement prediction may include model registration points, which may be used to define a spatial definition of the organ placement prediction. In this regard, according to some example embodiments, once the organ placement prediction is determined, the processing circuitry may be configured to align the spatial definition of the individual's body with the spatial definition of the organ placement prediction. To do so, for example, the coordinates of the model registration points may be positioned at the coordinates of the body registration points of the body. As such, for example, the organ placement prediction may have a first model registration point at a position of the right shoulder and a first registration point location may be defined at the position of the right shoulder of the individual's body. As such, the first model registration point may be set to the same spatial position as the first registration point location, thereby registering one portion of the organ placement prediction to the body. Such point mapping may be performed for a number of locations to complete the registration of the organ placement prediction with the body.

Figure 6:
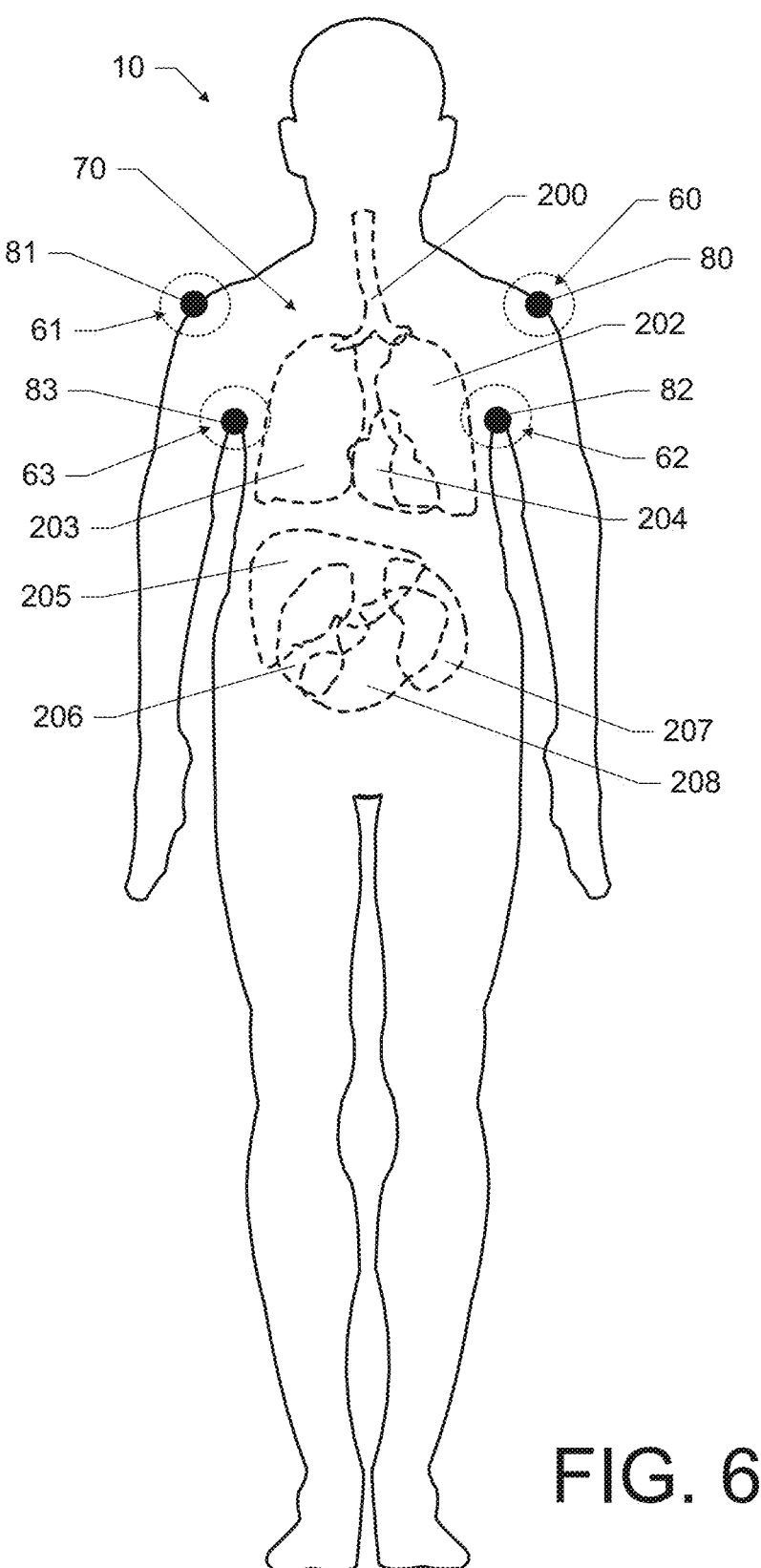
FIG. 6 illustrates a registered rendering of the organ placement prediction including a plurality of organs according to some example embodiments.

With reference to FIG. 6, the body 10 is shown with a rendering 70 of the position, size, and shape of organs from a determined organ placement prediction. For clarity, the body 10 is shown as the exterior of the physical body of the individual, and the rendering 70 is provided in visual combination with the body 10 as a virtual element (e.g., augmented reality element) to form a unified visualization. In this regard, an organ placement prediction has been determined and registered to the body 10. Accordingly, a visualization of the predicted position, size, and shape of the organs, based on the external anatomical measurements and the demographic characteristics is shown. As seen in FIG. 6, for example, various organs are shown, including the trachea 200, the left lung 202, the right lung 203, the heart 204, the liver 205, right kidney 206, the left kidney 207, and the stomach 208.

In association with registration of the rendering 70 of the organ placement prediction with the body 10, and according to some example embodiments, the body registration points 60, 61, 62, and 63 are shown as defined in FIG. 4. Additionally, corresponding model registration points 80, 81, 82, and 83, respectively, are shown. In this regard, for an example registration process, body registration points 60, 61, 62, and 63 may be used for registration and corresponding model registration points 80, 81, 82, and 83, respectively may be used for registration. In this regard, the model registration point 80 may be a left shoulder model registration point, model registration point 81 may be a right shoulder model registration point, model registration point 82 may be a left armpit registration point, and model registration point 83 may be a right armpit registration point. The model registration points may be points that are spatially defined relative to the organ position information, the organ size information, and the organ shape information for use as anchor points for spatially linking the organ placement prediction with the body 10. For registration of the organ placement prediction with the body 10, the model registration points may be aligned with and anchored to the body registration points such that organ placement prediction is maintained in a registered position with the body 10. As such, to register the organ placement prediction with the body 10, body registration point 60 may be aligned with and anchored to model registration point 80, body registration point 61 may be aligned with and anchored to model registration point 81, body registration point 62 may be aligned with and anchored to model registration point 82, and body registration point 63 may be aligned with and anchored to model registration point 83. Moreover, although body registration points 60, 61, 62, and 63 and corresponding model registration points 80, 81, 82, and 83 are visually depicted in FIG. 6, the body registration points 60, 61, 62, and 63 and model registration points 80, 81, 82, and 83 need not, and likely would not, be rendered with the rendering 70 of the organ placement prediction.

Figure 7:
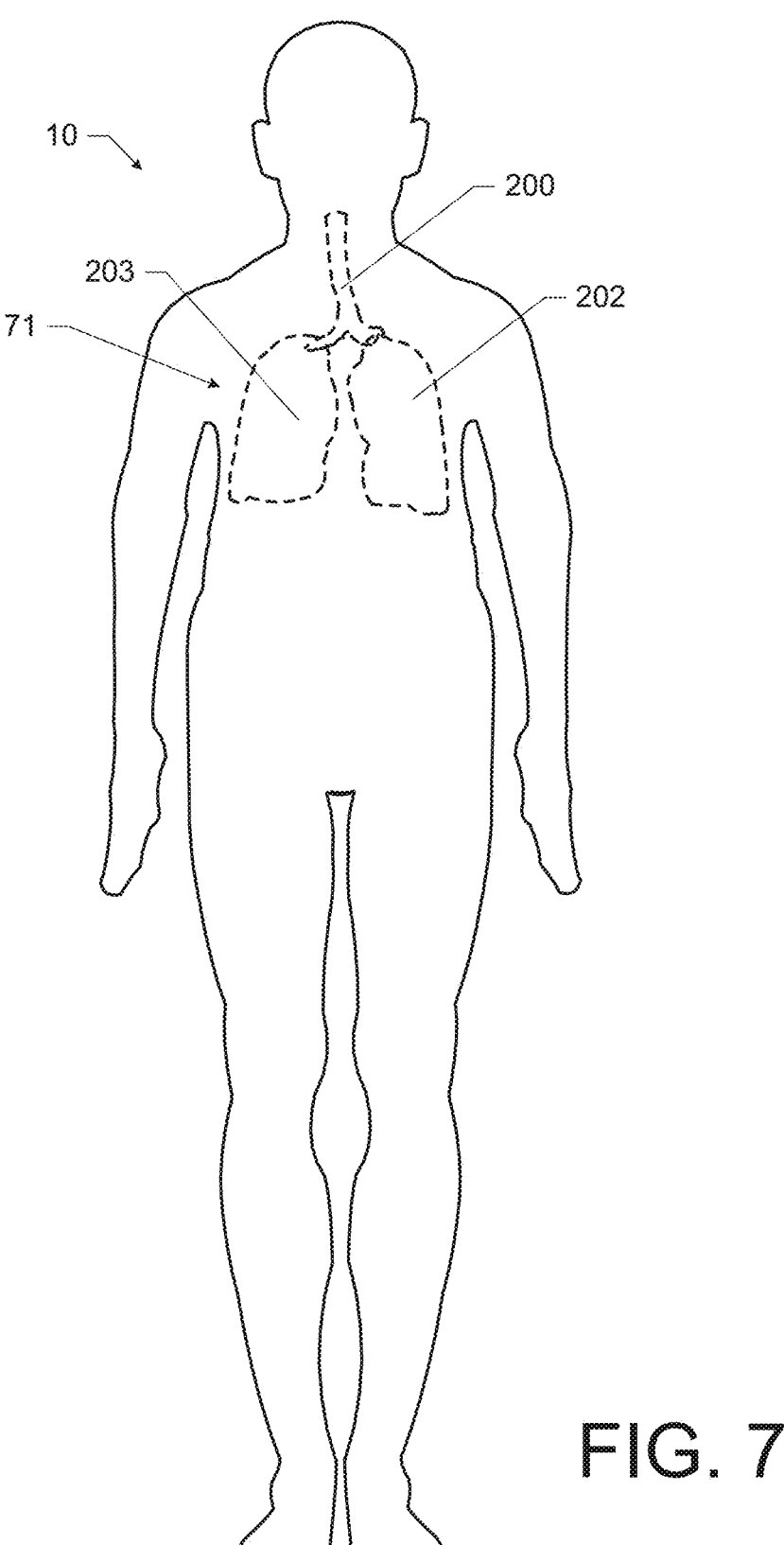
FIG. 7 illustrates a registered rendering of the organ placement prediction including respiratory organs according to some example embodiments.
Figure 8:
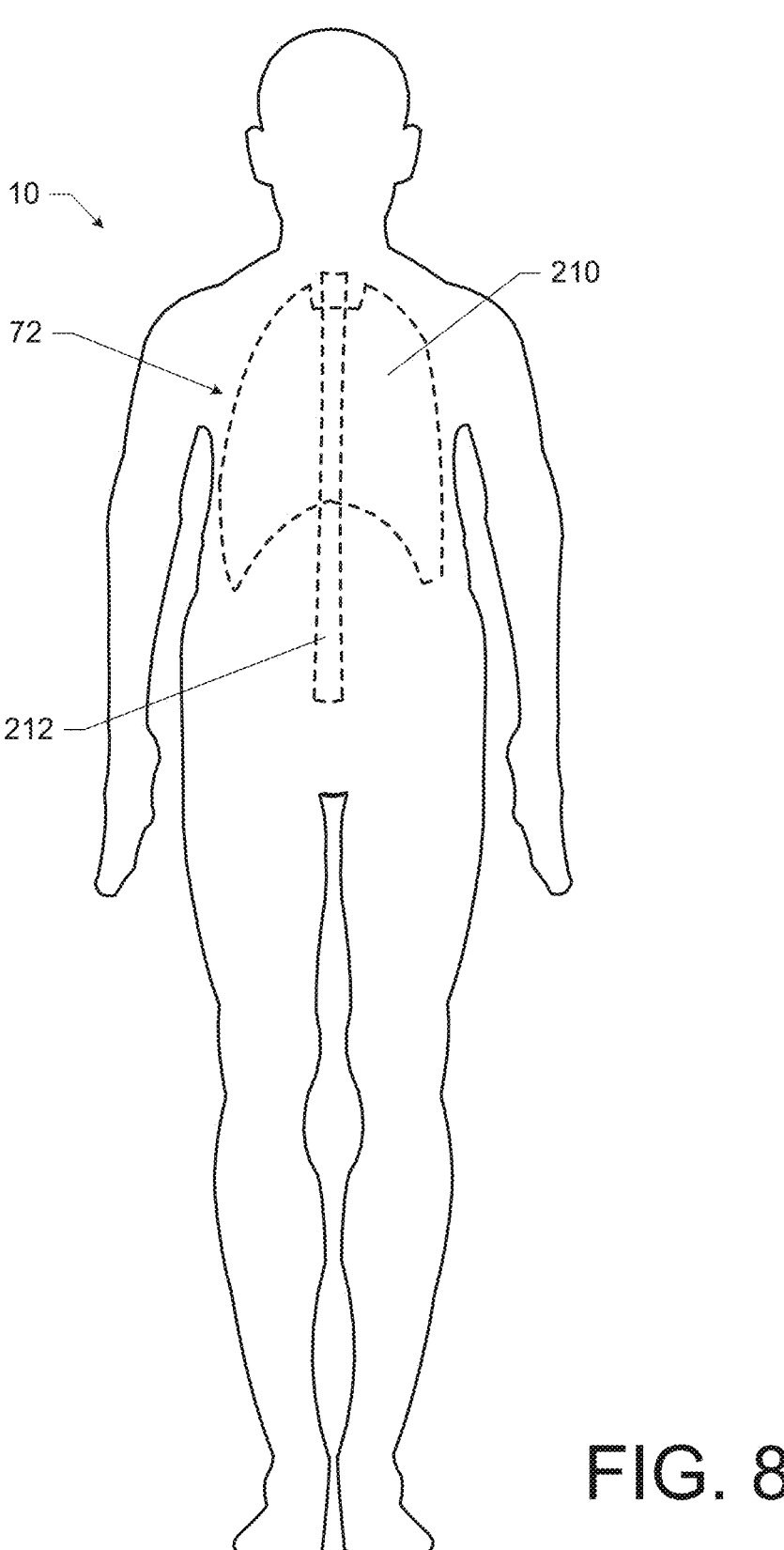
FIG. 8 illustrates a registered rendering of the organ placement prediction including skeletal structures or organs according to some example embodiments.
Figure 9:
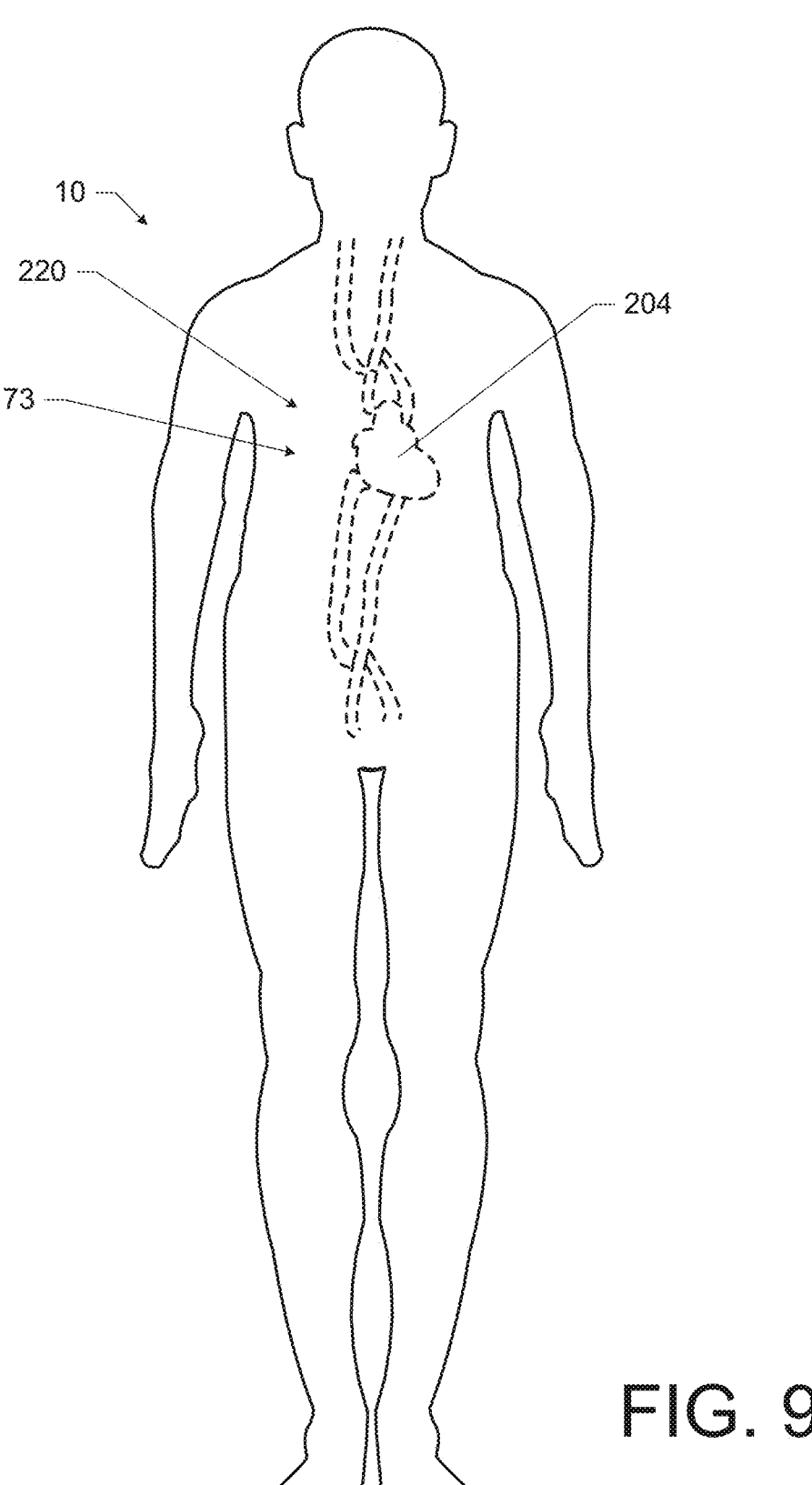
FIG. 9 illustrates a registered rendering of the heart and the vascular system according to some example embodiments.

As mentioned above, the organ placement prediction may include many organs, and the processing circuitry may be configured to permit selection of, for example, organ categories for isolated visualization. In this regard, as shown in FIG. 7, the respiratory organs have been selected, and, as such, only the trachea 200, and the lungs 202 and 203 are shown in the rendering 71. Similarly, in FIG. 8, the skeletal structures (or organs as defined herein) are shown. In this regard, the rib cage 210 and the spine 212 are shown in the rendering 72. Further, in FIG. 9, the vascular system has been selected. As such, the heart 204 is shown with arteries and veins 220 in the rendering 73.

Figure 10:
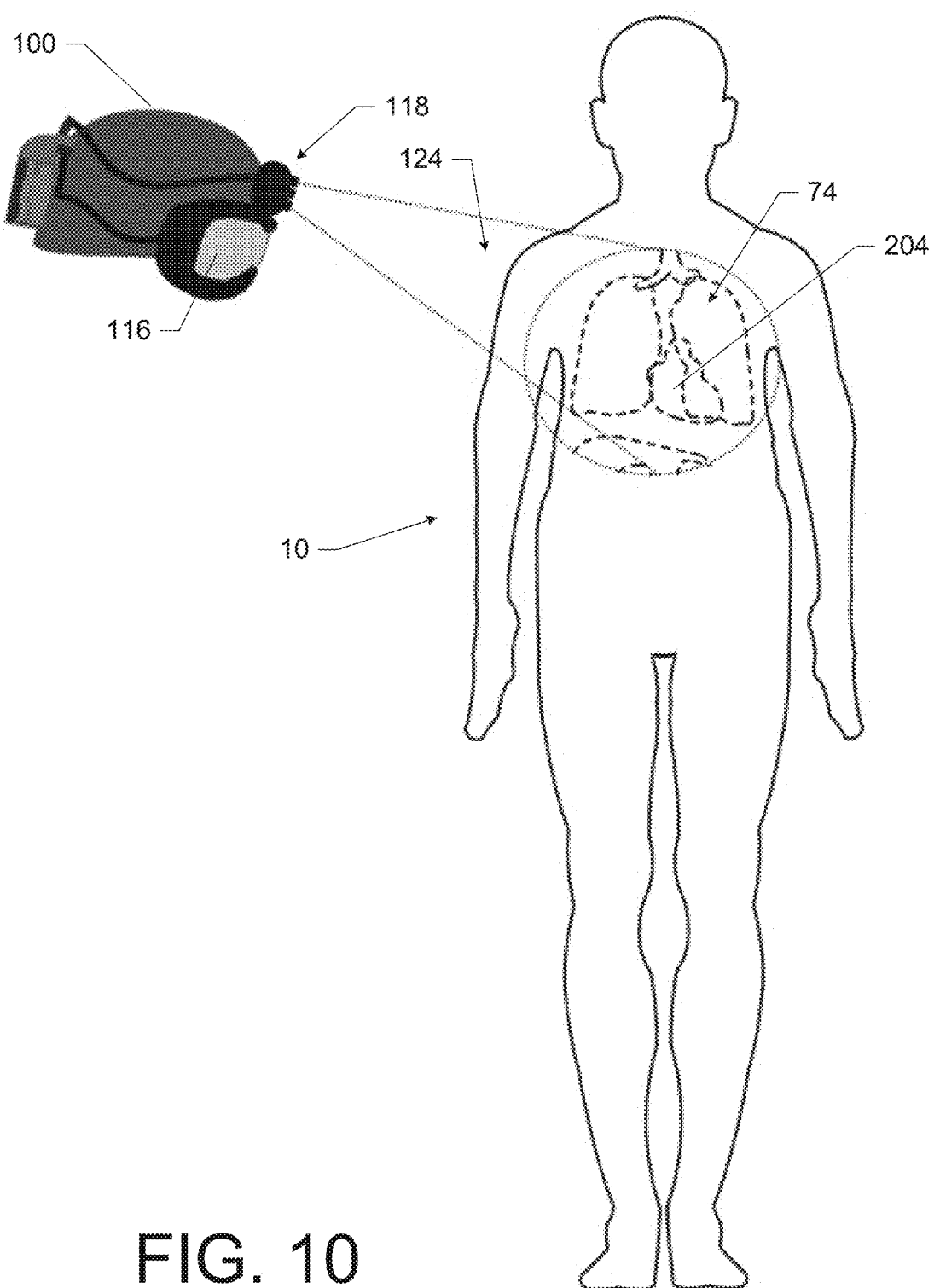
FIG. 10 illustrates an example body of an individual with an organ placement prediction rendered on the body within a field of view of the predictive internal anatomy visualization device according to some example embodiments.

While FIGS. 6-9 show the organ placement prediction without regard to the user's field of view it is understood that, as shown in FIG. 10, the field of view 124 of the sensors 118 may determine the portion of the organ placement prediction that is included in the augmented reality rendering 74 on the body 10. In this regard, as indicated in FIG. 10, the movement of the field of view 124 of the sensors 118 may result in a different portion of the organ placement prediction being rendered based on the direction of the field of view of the sensors and ultimately the user.

Additionally, according to some example embodiments, upon rendering the organ placement prediction, the processing circuitry of the headset 100 may permit the user to make various real-time adjustments to the organ placement prediction and the rendering of the organ placement prediction. In this regard, for example, local refinement of the organ placement prediction may be performed to improve the scaling of the organ placement prediction relative to the body 10. Such scaling, according to some example embodiments, may be performed in real-time and in a non-linear manner based on the organ placement prediction. Further, according to some example embodiments, the scaling may be XYZ or cubic scaling.

Figure 11:
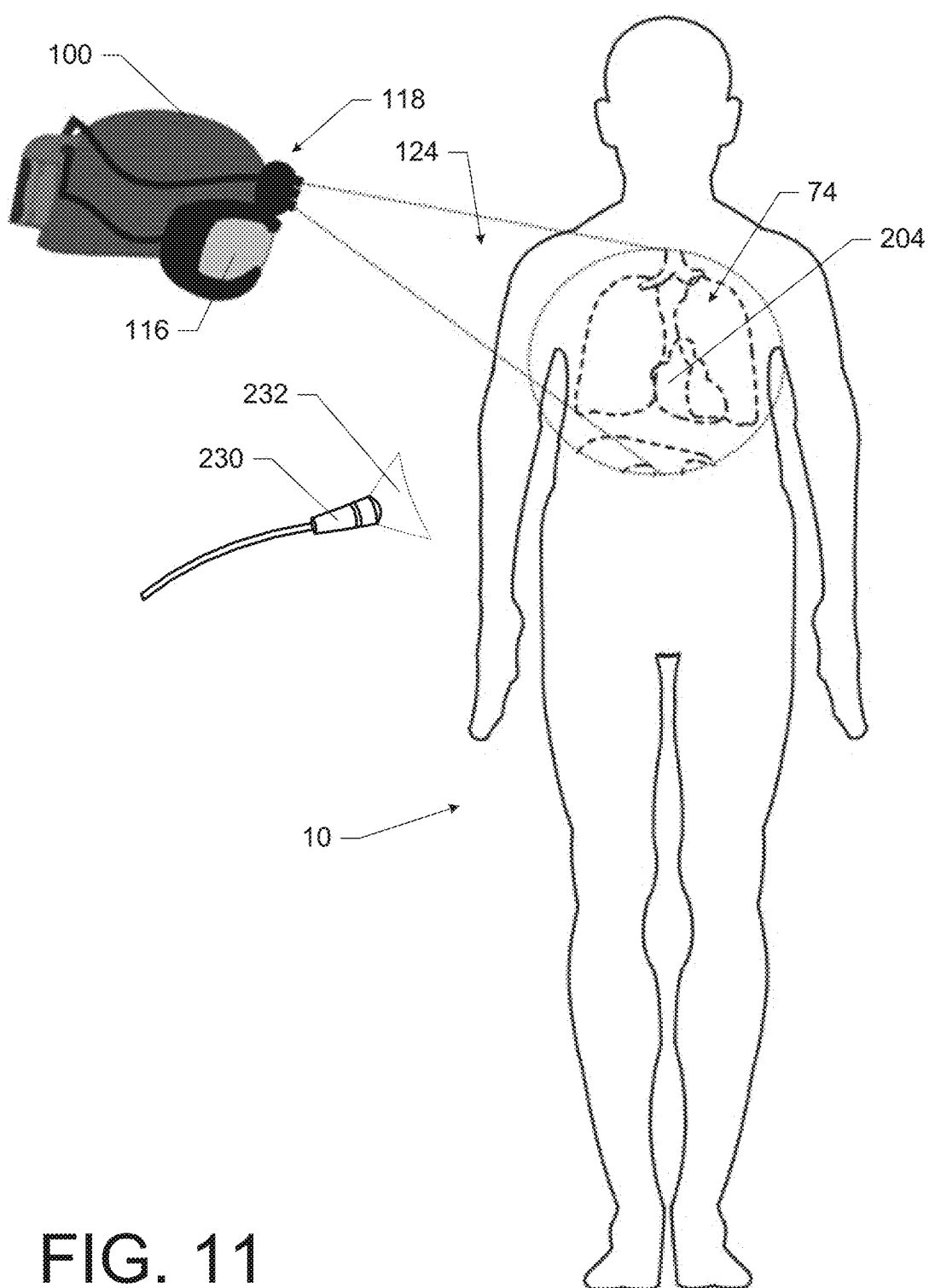
FIG. 11 illustrates an example body of an individual with an organ placement prediction rendered on the body within a field of view of the predictive internal anatomy visualization device for use with an ultrasound-imaging device according to some example embodiments.

As shown in FIG. 11, a healthcare implement may be employed in collaboration with the rendering of the organ placement prediction. As described below and otherwise herein, the rendering of an organ placement prediction may assist with the utilization of various healthcare implements when performing a procedure including, but not limited to, those described herein. In this regard, a healthcare implement may be identified by the processing circuitry, via captured images, based on, for example, a known shape of the healthcare implement to thereby determine a type of implement that is, for example, in the field of view of the sensors 118. According to some example embodiments, the healthcare implement may include markings or features that indicate a unique identifier for the healthcare implement. In this regard, the healthcare implement may include a barcode, QR code, RFID tag, or the like that may be read by a sensor 118 to determine an implement type for the healthcare implement (e.g., ultrasound-imaging device, infrared imaging device, needles including a collapsed lung needle, probes, scalpel, forceps, scissors, endoscope, catheter, stethoscope, tube, bandage, or the like). According to some example embodiments, the healthcare implement may be color-coded to indicate the type of implement, and the processing circuitry may be configured to determine the type of implement based on detection of its color.

Additionally, portions of a healthcare implement may be identifiable for position tracking purposes as further described below. In this regard, the type of implement may be determined as provided above, but an operating end or operating surface (e.g., a tip, cutting edge, sensor shield, or the like) of the healthcare implement may also be determined. According to some example embodiments, an operating end or surface may be determined by the processing circuitry via shape analysis when performing image capture processing from the sensors. According to some example embodiments, a set of markers on the healthcare implement may be identified or localized, and the set of markers (which may be provided via a three-dimensional printed frame structure, via reflective or retro-reflective elements, or the like) may be tracked to determine position and orientation, as well as track motion of the healthcare implement. However, in some example embodiments, the healthcare implement may include operating indicators at a location on the healthcare implement to indicate the operating end or surface. For example, an operating end or surface of a healthcare implement may, for example, be marked with a pattern or a color, or may include a detectable light source (e.g., an LED). Such markings may be readily identified via image processing by the processing circuitry for tracking purposes when providing procedure-related guidance as further described herein.

Referring back to FIG. 11, an example healthcare implement may be an ultrasound-imaging sensor 230 or portable X-ray device having a field of view 232. In an example scenario, the user of the headset 100 may wish to obtain ultrasound imaging of the individual's heart. According to some example embodiments, the organ placement prediction has been rendered with the body 10 to show the predicted position, size, and shape of the heart 204. As such, via visualization of the predicted position, size, and shape of the heart 204 on the display 116, the user may quickly place and orient the ultrasound-imaging sensor 230 at the predicted location of the heart 204 to assist in ultrasound imaging the actual heart of the individual. As such, the predicted location of the heart 204 may be used as a guide to quickly placing the ultrasound-imaging device 230 at or near the location of the actual heart.

Additionally, according to some example embodiments, the ultrasound-imaging device 230, as an example of a body-aligned apparatus for use with the organ placement prediction, may be configured to capture position-based healthcare information associated with the body of the individual. For example, the ultrasound-imaging device 230 may be configured to capture position-based information regarding the position, size, and shape of organs, such as, for example, the heart. Such position-based information regarding the interior anatomy of the body may be provided to processing circuitry for use in adjusting the registration and alignment of the organ placement prediction with the body 10. Additionally, the position-based information may be provided to processing circuitry for use in adjusting the scaling of the organ placement prediction. In this regard, for example, for a particular organ, e.g., the heart, the position, size, and shape of the heart as captured by the ultrasound-imaging device 230 may be compared to the position, size, and shape of the heart in the organ placement prediction, respectively. If the comparison identifies more than a threshold difference between the position, size, or shape of the organ as captured by the ultrasound-imaging device 230 and the same organ as described in the organ placement prediction, then the organ placement prediction may be adjusted to move, scale, or reshape the organ, and possibly other organs, within the organ placement prediction for the current individual. According to some example embodiments, based on the captured relative positioning of, for example, organs identified in the position-based data, all organs described by the organ placement prediction may be adjusted (e.g., shifted in position, scaled to be larger or smaller, changed in shape, the like) or, according to some example embodiments, only select organs may be adjusted. Such adjustments may be stored for use with organ placement prediction rendering of the specific individual in the future. Further, such position-based information may be provided, either locally or remote, to a machine learning algorithm for the body shape model to integrate the position-based information into the body shape model for further refinement as described above. In situations where a primary body shape model is remote, the position-based data or the updated body shape model may be uploaded for use by others. As such, for example, additional imaging devices may be used in real-time to further calibrate, align, and scale the organ placement prediction with the body 10, as well as further refine the body shape model.

The ultrasound-imaging device 230 may be one type of imaging device that may be implemented in accordance with various example embodiments. In this regard, any type of imaging device may prove useful for further investigating the internal anatomy of an individual's body. In this regard, according to some example embodiments, an infrared imaging device may be used in a manner similar to the ultrasound-imaging device 230. The infrared imaging device may identify, for example, common hot or cool spots, which may be used a position-based information. Additionally, according to some example embodiments, a photoplethysmography (PPG) sensor that detects colored light reflections (e.g., commonly used in smartwatch devices to measure heart rate) may be used in a manner similar to the ultrasound-imaging device 230 and position-based information from the PPG sensor may be provided in the same or similar manner.

Figure 12:
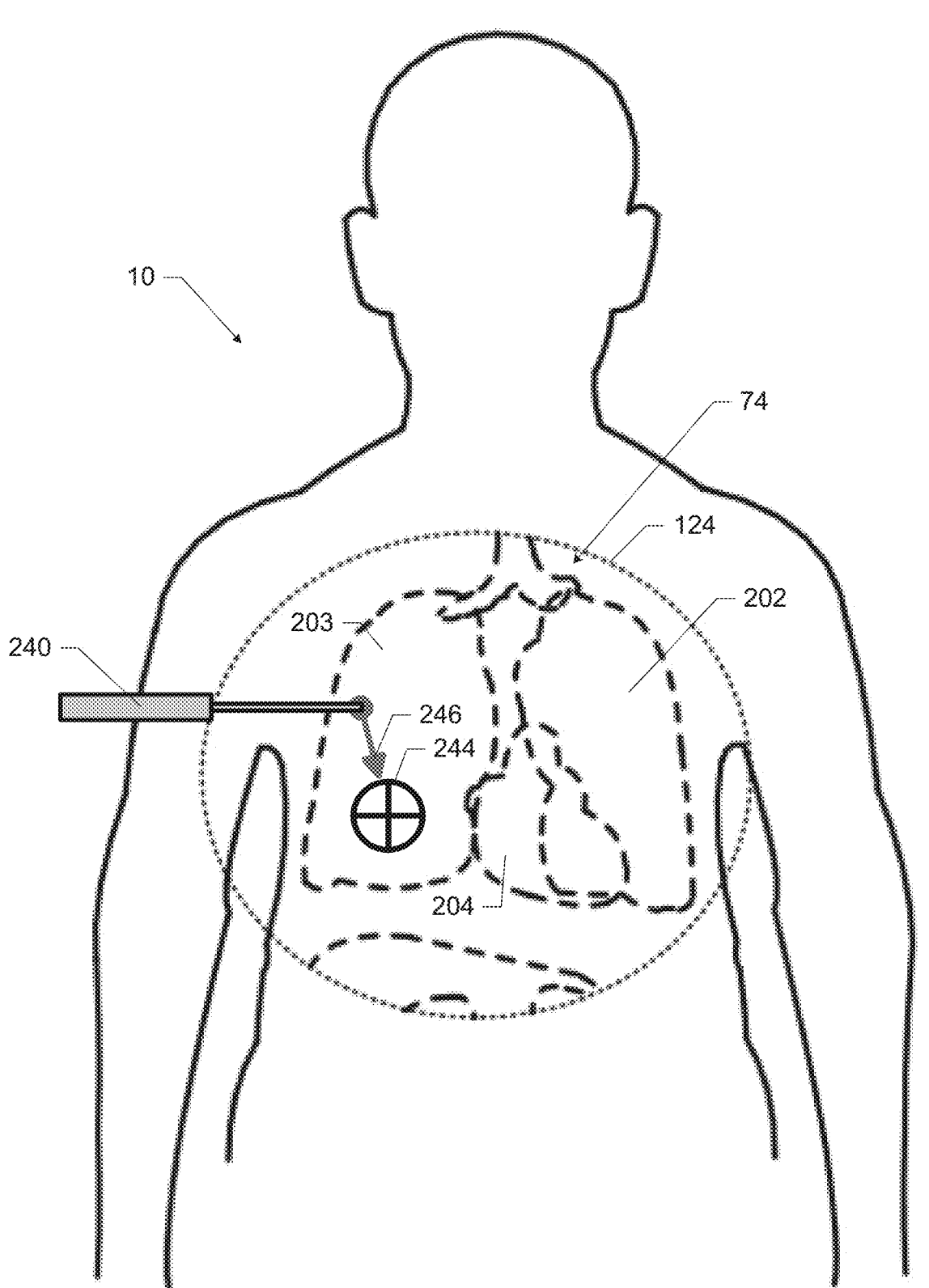
FIG. 12 illustrates an example body of an individual with an organ placement prediction rendered on the body within a field of view of the predictive internal anatomy visualization device for use with a collapsed lung needle according to some example embodiments.

As shown in FIG. 12, a healthcare implement in the form of a collapsed lung needle 240 is shown in association with an organ placement prediction rendering. In this regard, based on the field of view 124 of the sensors 118, a rendering of an organ placement prediction is provided in augmented reality on the body 10. Additionally, a target 244 is also shown, which may be provided based on a selected type of healthcare procedure. In this example case, the target 244 is positioned on the right lung 203 in what has been determined to be, by the processing circuitry, an interaction location for piercing the collapsed lung 203 to permit recovery of the collapsed lung 203. Such an interaction location may be determined based on healthcare procedure information that may be accessed in, for example, a remote healthcare database and is provided in association with a communicated diagnosis of the issue. Additionally, according to some example embodiments, since the collapsed lung needle 240 is within the field of view 124 and may have an indicator such as that can instruct the system as to what tool it is, the processing circuitry may identify the implement as the collapsed lung needle 240 (e.g., based on a bar code, QR code, or other indicator) and also determine a position of the needle 240, or more specifically a tip of the needle 240.

Additionally, the processing circuitry may be configured to further assist the user by providing a guidance indicator (arrow) 246, based on the determined position of the needle 240, that indicates a direction for the user to move the needle 240 to place the needle 240 at the target 244. Once the needle 240 is in position, the user may perform the healthcare procedure with respect to the right lung 203. According to some example embodiments, rather than the needle 240, a training tool may be used in a training context to determine whether a trainee is properly positioning the training tool when practicing to perform and actual healthcare procedure.

Use of the collapsed lung needle 240 in association with the rendering 74 of the organ placement prediction is but one example procedure that may benefit from, or even be enabled by, some example embodiments. In this regard, based on a diagnosis, the user may select a healthcare procedure to be performed via a user interface, the processing circuitry of, for example, the headset 100, may receive the selection. In response to receiving the healthcare procedure selection, the processing circuitry may be configured to retrieve, locally or remotely, healthcare procedure information including an interaction location on the body for performing the healthcare procedure. According to some example embodiments, the healthcare procedure information may also include instructions, which may be provided to the user, for example, as video or audio instructions on how to perform the procedure in conjunction with the interaction location. Accordingly, the processing circuitry may be further configured to determine a registered interaction location, based on the retrieved interaction location and the organ placement prediction that has also been registered to the body 10. In this regard, the interaction location may be defined as a location relative to features (e.g., organs or the like) that may be defined, and possibly named, in the organ placement prediction. As such, via a common coordinate system, the registered interaction location can be determined relative to the organ placement prediction and the body 10. Upon determining the registered interaction location, the processing circuitry may be configured to render an interaction target with the organ placement prediction on the body 10, with guidance indicators for moving a determined healthcare implement, as necessary, during performance of the procedure. According to some example embodiments, the processing circuitry may also detect an orientation or direction of movement of the healthcare implement, e.g., an angle of entry into the body 10, and the processing circuitry may output feedback (e.g., visual or audible) as the user is performing the procedure to adjust the position of the healthcare implement in real-time.

Following from the above, according to some example embodiments, another example procedure that may benefit from example embodiments is a needle chest decompression procedure. A needle chest decompression procedure may be performed to treat a tension pneumothorax, which is currently the second leading cause of death in a combat setting. As such, upon diagnosing a tension pneumothorax, the user may make a corresponding selection via the headset 100. As such, the processing circuitry, responsive to the selection, may retrieve the healthcare procedure information for the needle chest decompression procedure, and the processing circuitry may, based on the healthcare procedure information, be configured to assist the user with a needle chest decompression procedure. For a needle chest decompression procedure, a large-bore needle or catheter (e.g., a 10 to 14 gauge needle or catheter) may be inserted, on the affected side of the chest, between the second intercostal space (i.e., between the second and third ribs), a third intercostal space (i.e., between the third and fourth ribs), and the midclavicular line with the tip of the needle entering through the individual's skin above and adjacent to the third rib margin. This positioning information may be included in the healthcare procedure information for the needle chest decompression procedure. As such, the processing circuitry may be configured to determine the registered interaction location, based on the healthcare procedure information and the registered organ placement prediction, and render a target at the registered interaction location. When determining the registered interaction location, the processing circuitry may also be configured to evaluate a risk factor for performing the procedure based on a proximity of critical organs (e.g., the heart) to the registered interaction location. According to some example embodiments, if the proximity of the registered interaction location is within a threshold proximity (e.g., within a threshold distance), the processing circuitry may be configured to output an indication or degree of the risk to the user or indicate that the individual is not a candidate for the procedure due to the evaluation of the procedure as provided in the healthcare procedure information in combination with the organ placement prediction for the individual.

The processing circuitry may also be configured to provide visual or audible instructions to the user regarding performance of the needle chest decompression procedure. Additionally, as mentioned above, as the user moves the needle or catheter into position, the processing circuitry may render guidance indications to visually assist the user with performing the procedure.

Additionally, as the user inserts the needle or catheter into the body, the processing circuitry may receive real-time images (e.g., 3D scans) for processing, evaluate an orientation and direction of movement (e.g., an angle of entry or angle of movement), and provide visual or audible feedback to the user based on a comparison of the desired orientation and direction of movement and the actual orientation and direction of movement. For example, the needle or catheter for the needle chest decompression procedure should be inserted at a ninety-degree angle to the chest cavity. As such, if the angle of entry or angle of movement relative to the chest cavity is more than a threshold difference (e.g., five degrees), then a video or audible alert may be provided to the user so that the use may adjust the orientation or direction of movement accordingly.

Additionally, according to some example embodiments, a depth of insertion may be included in the healthcare procedure information. Again, the processing circuitry may be configured to receive real-time images (e.g., 3D scans) for processing, evaluate a depth of insertion, and provide visual or audible feedback to the user based on a comparison of the desired depth of insertion and the actual depth of insertion. In some example embodiments, the healthcare implement may include gradations on the portion of the implement that is inserted into the body, and, based on the gradations, a depth of insertion may be determined via image processing. In this regard, the processing circuitry may be configured to determine the desired depth of insertion based on the healthcare procedure information and the organ placement prediction. More specifically, for the needle chest decompression procedure, the needle or catheter should pierce into the pleura or pleural cavity. The organ placement prediction may include a prediction of the depth of the pleura or pleural cavity, and, as a result, the desired depth of insertion may be determined. Accordingly, as the user inserts the healthcare implement, i.e., the needle or catheter, the processing circuitry receive the real-time images (e.g., 3D scans), evaluate a depth of insertion, and provide visual or audible feedback to the user indicative of a current actual depth of the healthcare implement and adjust the visual or audible feedback when healthcare implement reaches the desired depth of insertion. According to some example embodiments, a frequency of an audible tone may change as the actual depth of insertion changes or a frequency of pulse sounds may change as the actual depth of insertion changes. Additionally or alternatively, success sound (e.g., a bell or continuous tone) may be output when the actual depth of insertion is reached.

Another example procedure that may benefit from example embodiments is a chest tube insertion procedure. A chest tube insertion procedure may be installed to evacuate air, fluid, or blood from the pleural space in the chest. As such, upon diagnosing the need for a chest tube insertion procedure, the user may make a corresponding selection via the headset 100. As such, the processing circuitry, responsive to the selection, may retrieve the healthcare procedure information for the chest tube insertion procedure, and the processing circuitry may, based on the healthcare procedure information, be configured to assist the user with the chest tube insertion procedure. For the chest tube insertion procedure, a skin incision is made and then large forceps are be inserted through the intercostal muscles to puncture the parietal pleura to enlarge the opening and clamp open. The procedure can have a risk of inadvertently puncturing the lung or damaging intercostal nerves and vessels.

The positioning, orientation and direction of insertion, and depth of insertion information may be included in the healthcare procedure information for performing each of the operations of a chest tube insertion procedure. In this regard, a two to three centimeter transvers incision may be made on the body at the anterior axillary line over the fourth and fifth intercostal space. The incision may be extended to intercostal muscles. The opening should be clamped open with a diameter of about one and a half or two centimeters.

As such, the processing circuitry may be configured to determine the registered interaction location for the incision, as described above, based on the healthcare procedure information and the registered organ placement prediction. The processing circuitry may then render a target at the registered interaction location. In this regard, because the procedure involves an incision rather than a needle puncture, a rendering of a virtual incision at the registered interaction location upon completion of the actual incision. In this regard, based again on the healthcare procedure information, a desired length of the incision may be rendered that can allow the user to simply trace the virtual incision with a scalpel to make the incision. Following from the description above, the processing circuitry may be configured to evaluate the position, length, and depth of the incision, and provide visual or audible feedback regarding the same in real-time to the user performing the procedure. As mentioned above, the processing circuitry may be configured to evaluate a risk factor for performing the procedure based on a proximity, for example, of the lung to the registered interaction location, and a risk indication feedback may be provided via the user interface in response to the proximity evaluation.

Based on the healthcare procedure information, the processing circuitry may provide video or audible instructions to the user to insert the forceps. Again, the processing circuitry may be configured to a desired length of the incision may be rendered that can allow the user to simply trace the virtual incision with a scalpel to make the incision. Following from the description above, the processing circuitry may be configured to evaluate the position and depth of insertion for the forceps, and provide visual or audible feedback regarding the same in real-time to the user performing the procedure. After clamping the opening, the processing circuitry may provide video or audible instructions to insert a tube, with the depth of insertion being evaluated for the provision of feedback to the user.

Yet another example procedure that may benefit from example embodiments is an intraosseous access procedure using a sterile needle. An intraosseous access procedure may be performed to deliver rapid fluid resuscitation or pharmaceutical treatment when standard intravenous (IV) access is not readily accessible. Upon diagnosing the need for an intraosseous access procedure, the user may make a corresponding selection via the headset 100. As such, the processing circuitry, responsive to the selection, may retrieve the healthcare procedure information for the intraosseous access procedure, and the processing circuitry may, based on the healthcare procedure information, be configured to assist the user with the intraosseous access procedure. Following from the functionalities described above, the processing circuitry may be configured to render a target at the registered interaction location and monitor the procedure to provide feedback regarding the same to the user via the user interface of the headset 100.

In determining the registered interaction location for the intraosseous access procedure, the processing circuitry may be configured to determine the registered interaction location as a sternal insertion site that is located midline (approximately one to two centimeters) below the sternal notch. An incision is made in alignment with the suprasternal notch, with the incision being less than three millimeters. The sterile needle is inserted perpendicular to a plane of the manubrium to penetrate the bone cortex and ceasing further insertion upon a sudden lack of resistance due to entry into the medullary space. Based on the description above, similar renderings, instructions, monitoring, and feedback on the intraosseous access procedure may be provided by the processing circuitry via the user interface.

Figure 13:
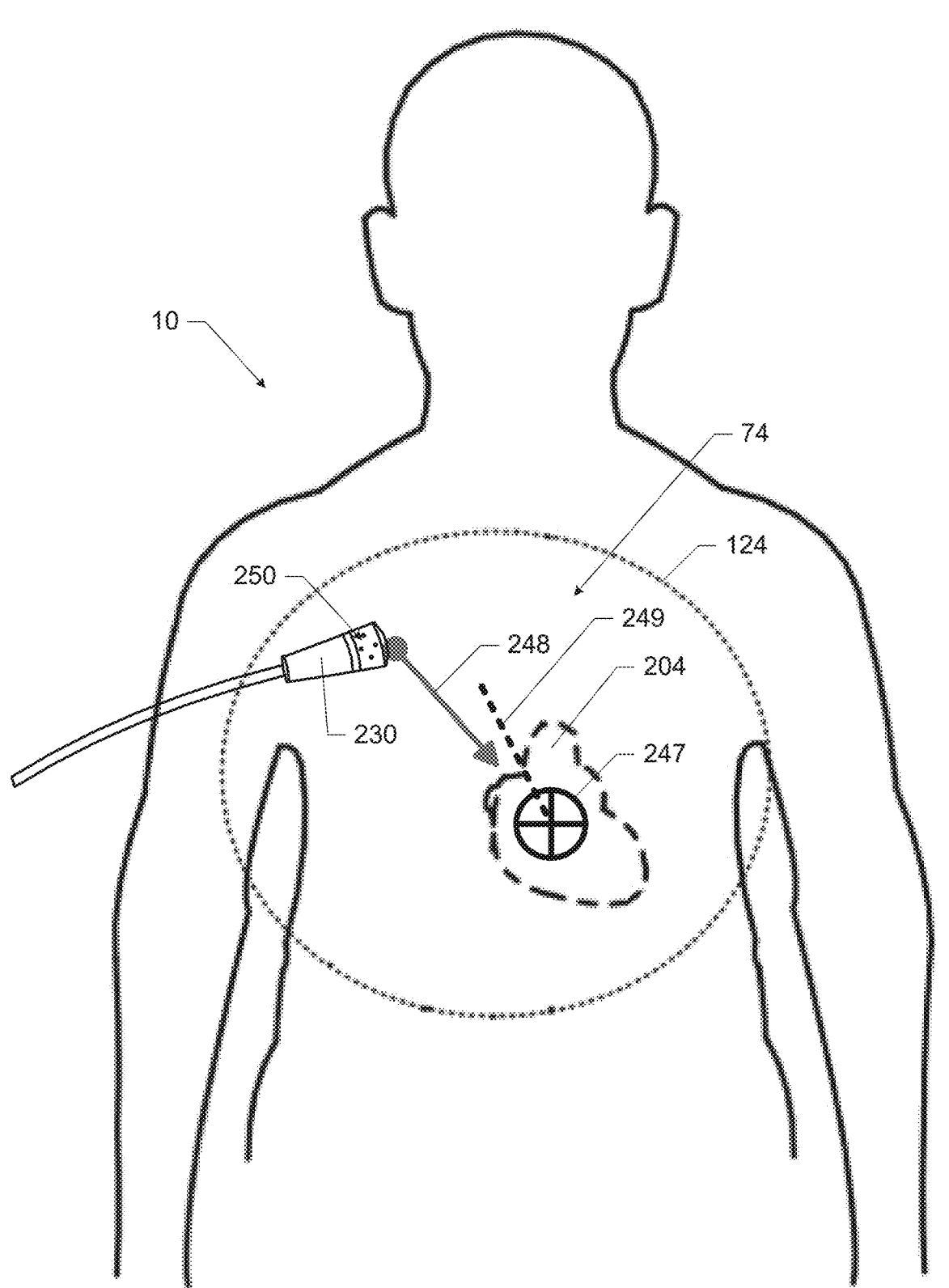
FIG. 13 illustrates an example body of an individual with an organ placement prediction rendered on the body within a field of view of the predictive internal anatomy visualization device for use with an ultrasound-imaging device according to some example embodiments.

Following from the ultrasound imaging sensor example shown in FIG. 11, a more detailed illustration of an implementation of the ultrasound-imaging sensor 230 is shown in FIG. 13 as another healthcare implement that may be used in association with the augmented reality rendering of the heart 204. The position and orientation of the ultrasound-imaging sensor 230 is determined using markers placed on the probe that uniquely identify and localize the sensors, and it is shown in association with the heart 204 provided in association with an organ placement prediction rendering. In the example shown in FIG. 13, the user may have selected that only the heart 204 be shown in the augmented reality rendering. Again, the user may have selected a healthcare procedure of ultrasound imaging the heart of the individual. As such, the processing circuitry is configured to render a target 247 at the location of the heart 204 on the display 116. The target 247 may be an indicator of where the ultrasound imaging sensor 230 should be positioned to capture desired images of the heart 204 in support of a given procedure. According to some example embodiments, in addition to the target 247, an orientation target 249 may also be generated and rendered to assist a user with orienting the healthcare implement for performing the procedure. In this regard, for example, the orientation target 249 may be a line that is rendered from the target 247 to indicate an angle for the orientation target 249. Accordingly, the processing circuitry may be configured to measure an orientation of the healthcare implement (e.g., via orientation markings 250 on the healthcare implement, in this case, the ultrasound-imaging sensor 230) relative to the line of the orientation target 249. Via this determined relative orientation, an orientation assessment may be performed, for example, repeatedly, and when the orientation of the healthcare implement is within a threshold angle with the orientation target 250, an alert or notification can be provided via a user interface indicating, for example, that a proper position and orientation have been achieved. Since the ultrasound-imaging sensor 230 is within the field of view 124, the processing circuitry may determine a position of the ultrasound-imaging sensor 230. The processing circuitry may be further configured to further assist the user by providing a guidance indicator (arrow) 248 that indicates a direction for the user to move the ultrasound-imaging sensor 230 to place the sensor at the target 247. Once the ultrasound-imaging sensor 230 is in position, the user may perform ultrasound imaging of the actual heart and/or the predicted area for the heart of the individual. Data received from ultrasound-imaging sensor 230 may be used in real-time to further calibrate, align, and scale the heart 204 and other organ placement with the body 10.

Figure 14:
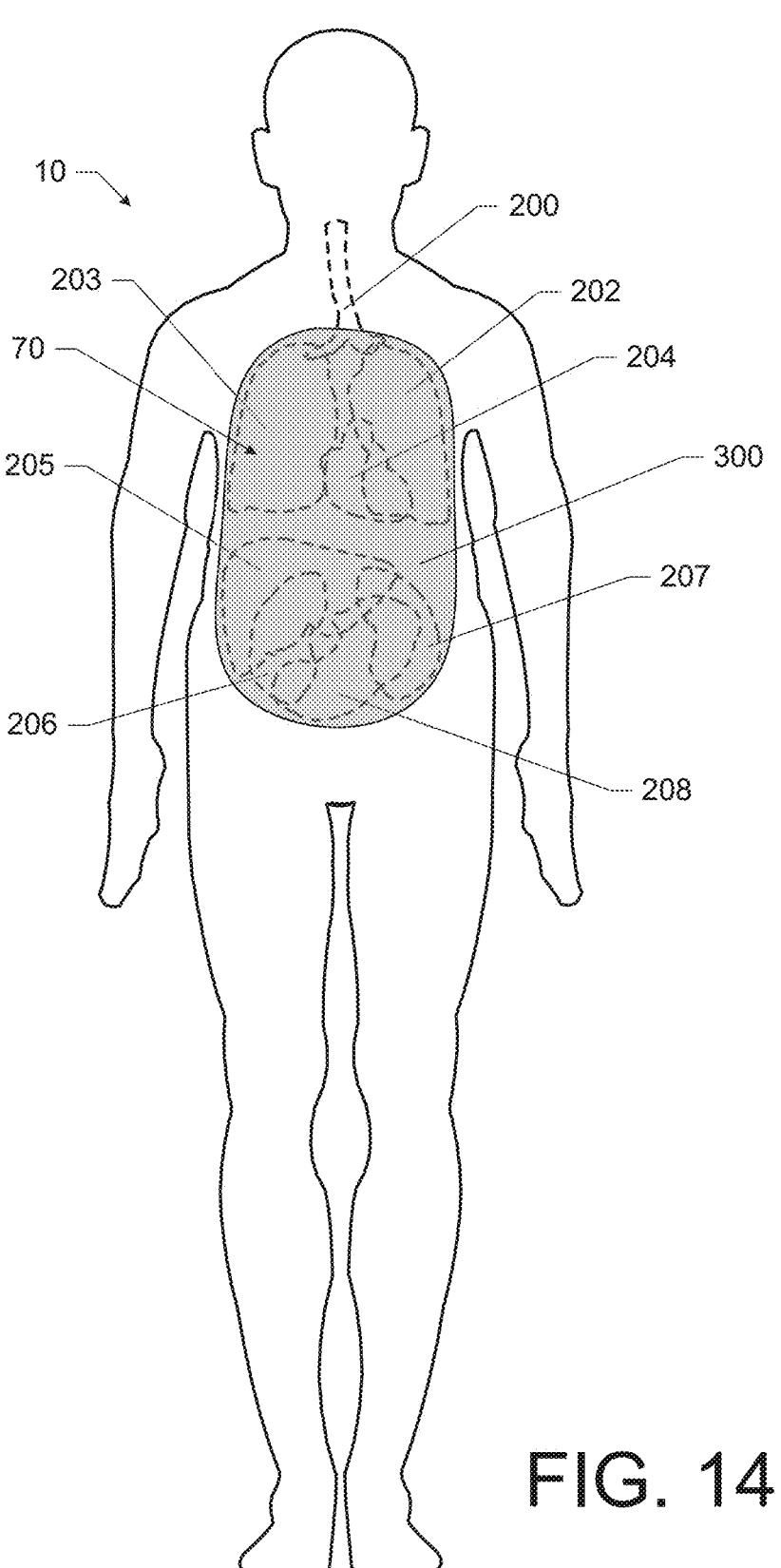
FIG. 14 illustrates an example body of an individual with an organ placement prediction rendered on the body and a protective body shield plate according to some example embodiments.

While various example embodiments have been described with respect to the provision of healthcare procedures, the rendering of an organ placement prediction for a given individual may also be useful in a number of other contexts that may benefit from knowing a predicted position, size, and shape of organs. In this regard, according to some example embodiments, such a predictive anatomy visualization may also be useful in the context of the design of personal protective equipment (PPE) that is specifically tailored for the individual. After determining an organ placement prediction for an individual, a procedure for determining a design of a PPE form-factor for example, for body armor plates may be employed. In this regard, for example, a body armor plate may be formed of a heavy material, and therefore efficient design and placement may be valuable. As shown in FIG. 14, an organ placement prediction may be determined and rendered on the body 10. Based on a perimeter defined by the outer extents of critical organs, a body armor plate 300 may be designed that contours to the perimeter shape to cover the critical organs for protection, while also limiting the size of the body armor plate to only cover those critical organs. By using the predicted location of the organs, a body armor plate 300 may be designed that is tailored to the internal organ position, size, and shape.

As mentioned above, in some instances, it is desirable for the amount of material used to form the PPE to be minimized. By minimizing the amount of material, the cost, weight, exposure to the material, and other parameters may be desirably minimized. For example, reduced weight may improve maneuverability and comfort. As such, in some example embodiments, extremely tailored PPE form-factors may be defined for individuals using a determined organ placement prediction for that individual. Again, such highly tailored form factors may be determined based on, for example, external anatomical measurements, without the need for, for example, x-ray or MRI imaging of the individual. In this regard, each organ and the criticality of protection of that organ may be considered in the design of the PPE form-factor. For example, in some instances, a PPE form-factor may be designed specifically for use as ballistics protection that only protects those organs that, injury to which, by a bullet would be life-threatening within ten minutes of an injury. In this regard, multiple separate piece components may be implemented for the PPE form-factor. Additionally, based on the position and depth of a critical organ, a thickness of the PPE form-factor may be determined. In other words, a thicker PPE element may be used to protect organs that are closer to the surface of the skin and a thinner PPE element may be used to protect organs that are more deeply positioned within the body. In some example embodiments, different materials may be used based on a position of critical organs. For example, a more expensive and higher performing material may be used in the PPE-form factor to protect critical organs, while non-critical organs may be protected by a less expensive material.

The above examples are just some example procedures that may benefit from the implementation of some example embodiments. Another example procedure is an extended focused assessment with sonography in trauma (E-FAST) exam. Via an E-FAST exam, for example, an assessment of internal bleeding or fluid build-up that may be identified using, for example, an ultrasound imaging device or the like. An E-FAST exam may involve the use of a healthcare implement, such as an ultrasound imaging device 230, and track its position via markings or the like.

Figure 15:
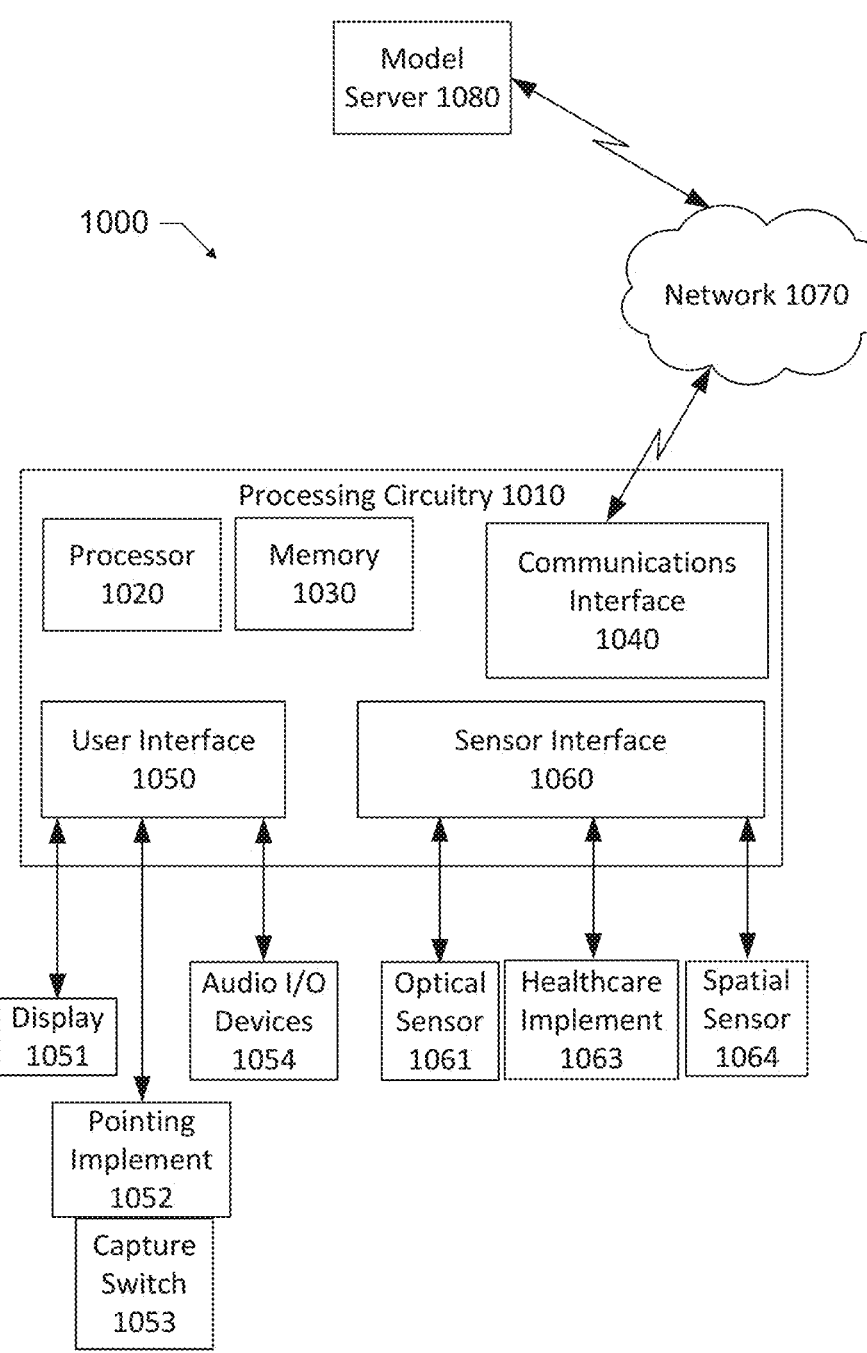
FIG. 15 illustrates an example block diagram of a predictive internal anatomy visualization device according to some example embodiments.

Now referencing FIG. 15, a block diagram of an example predictive internal anatomy visualization device 1000 is shown. In this regard, the device 1000 may comprise processing circuitry 1010, which may be operably coupled to a plurality of peripheral devices including sensors. Processing circuitry 1010 may comprise a processor 1020, a memory 1030, a user interface 1050, and a communications interface 1040. Additionally, the predictive internal anatomy visualization device 1000 may include additional components not shown in FIG. 15 and the processing circuitry 1010 may be operably coupled to other components of the predictive internal anatomy visualization device 1000 that are not shown in FIG. 15.

Further, according to some example embodiments, processing circuitry 1010 may be in operative communication with or embody, the memory 1030, the processor 1020, the user interface 1050, and the communications interface 1040. Through configuration and operation of the memory 1030, the processor 1020, the user interface 1050, and the communications interface 1040, the processing circuitry 1010 may be configurable to perform various operations as described herein, including the operations and functionalities described with respect to the processing circuitry of the headset 100. In this regard, the processing circuitry 1010 may be configured to perform computational processing, memory management, user interface control and monitoring, manage remote communications, and perform spatial image analysis according to an example embodiment. In some example embodiments, the processing circuitry 1010 may be embodied as a chip or chip set. In other words, the processing circuitry 1010 may comprise one or more physical packages (e.g., chips) including materials, components or wires on a structural assembly (e.g., a baseboard). The processing circuitry 1010 may be configured to receive inputs (e.g., via peripheral components), perform actions based on the inputs, and generate outputs (e.g., for provision to peripheral components). In an example embodiment, the processing circuitry 1010 may include one or more instances of a processor 1020, associated circuitry, and memory 1030. As such, the processing circuitry 1010 may be embodied as a circuit chip (e.g., an integrated circuit chip) configured (e.g., with hardware, software or a combination of hardware and software) to perform operations described herein.

In an example embodiment, the memory 1030 may include one or more non-transitory memory devices such as, for example, volatile or non-volatile memory that may be either fixed or removable. The memory 1030 may be configured to store information, data, applications, instructions or the like for enabling, for example, the functionalities described with respect to the headset 100 and as otherwise described. The memory 1030 may operate to buffer instructions and data during operation of the processing circuitry 1010 to support higher-level functionalities, and may also be configured to store instructions for execution by the processing circuitry 1010. The memory 1030 may also store various information including body shape model, measurement datasets, and the like. According to some example embodiments, various data stored in the memory 1030 may be generated based on other data and stored or the data may be retrieved via the communications interface 1040 and stored in the memory 1030.

As mentioned above, the processing circuitry 1010 may be embodied in a number of different ways. For example, the processing circuitry 1010 may be embodied as various processing means such as one or more processors 1020 that may be in the form of a microprocessor or other processing element, a coprocessor, a controller or various other computing or processing devices including integrated circuits such as, for example, an ASIC (application specific integrated circuit), an FPGA, or the like. In an example embodiment, the processing circuitry 1010 may be configured to execute instructions stored in the memory 1030 or otherwise accessible to the processing circuitry 1010. As such, whether configured by hardware or by a combination of hardware and software, the processing circuitry 1010 may represent an entity (e.g., physically embodied in circuitry—in the form of processing circuitry 1010) capable of performing operations according to example embodiments while configured accordingly. Thus, for example, when the processing circuitry 1010 is embodied as an ASIC, FPGA, or the like, the processing circuitry 1010 may be specifically configured hardware for conducting the operations described herein. Alternatively, as another example, when the processing circuitry 1010 is embodied as an executor of software instructions, the instructions may specifically configure the processing circuitry 1010 to perform the operations described herein.

The communications interface 1040 may include one or more interface mechanisms for enabling communication with other devices, networks, or servers, external to the processing circuitry 1010, via, for example, network 1070, which may, for example, be a local area network, the Internet, or the like, through a direct (wired or wireless) communication link to another external device, or the like. In some cases, the communications interface 1040 may be any means such as a device or circuitry embodied in either hardware, or a combination of hardware and software that is configured to receive or transmit data from/to devices in communication with the processing circuitry 1010. The communications interface 1040 may be a wired or wireless interface and may support various communications protocols (WIFI, Bluetooth, cellular, or the like). According to some example embodiments, the communications interface 1040 may support connection to, for example, a model server 1080, which may store a version of the body shape model. In this regard, according to some example embodiments, to ensure that the body shape model is current, the processing circuitry 1010 may use the body shape model in a remote fashion by providing, for example, external anatomical measurements and demographic characteristics to the remote body shape model on the model server 1080, and the model server 1080 may process the inputs and provide an organ placement prediction to the processing circuitry 1010 via the communications interface 1040.

The user interface 1050 may be controlled by the processing circuitry 1010 to interact with peripheral components or devices that can receive inputs from a user or provide outputs to a user. In this regard, via the user interface 1050, the processing circuitry 1010 may be configured to receive inputs from an input device, which may be, for example, a touch screen, a keyboard, keypad, a mouse, or the like. Moreover, the user interface 1050 may be configured to control the display 1051, which may be the same or similar to the display 116. Further, the user interface 1050 may be configured to control the operation of audio I/O devices 1054, which may include a microphone and a speaker. Further, according to some example embodiments, the pointing implement 1052, which may be same or similar to the pointing implement 130, may be operably coupled to the processing circuitry 1010 as a user interface device. However, according to some example embodiments, the pointing implement 1052 may be connected to the processing circuitry 1010 via, for example, a Bluetooth connection that may involve the communications interface 1040. Following from the description above, the pointing implement 1052 may include a capture switch 1053. The user interface 1050 may also be configured to provide control and outputs to peripheral devices such as, for example, a display 1051 (e.g., an over-eye display), speaker, or the like. The user interface 1050 may also produce outputs, for example, as visual outputs on a display, audio outputs via a speaker, or the like.

Moreover, the processing circuitry 1010 may also include a sensor interface 1060 that operates to control various sensors that may be operably coupled to the sensor interface 1060. In this regard, the sensor interface 1060 be a component of or include a sensor assembly (e.g., sensor assembly 114). Further, the sensor interface 1060 may be operably coupled to an optical sensor 1061, a healthcare implement 1063, and a spatial sensor 1064.

The spatial sensor 1064 may be circuitry configured to determine a current position and orientation of the predictive internal anatomy visualization device 1000. Further, the spatial sensor 1064 may be configured to determine orientation with respect to, for example, pitch, roll, and yaw. The position and orientation as determined by the spatial sensor 1064 may be components of spatial information. The spatial sensor 1064 may, for example, include circuitry (including for example, antennas) configured to capture wireless signals that may be used for determining a position of the spatial sensor 1064 based on the signals. In this regard, the spatial sensor 1064 may be configured to receive global positioning system (GPS) signals to determine a position. Additionally or alternatively, the spatial sensor 1064 may be configured to determine a position using locating techniques such as received signal strength, time of arrival, or the like. As mentioned above, the spatial information captured by the spatial sensor 1064 may be used in conjunction with captured images of, for example, an individual's body. According to some example embodiments, rather than measuring position or orientation directly via sensors that consider absolute position and orientation (i.e., relative to the Earth), the processing circuitry 1010 may be configured to determine a relative position or a relative orientation to, for example, the body 10. In this regard, based on the relative positions of body registration points or measurement positions, as indicated by the user and captured as described above, the relative position and relative orientation of, for example, the optical sensor 1061 be determined and used in the same manner as the spatial sensor 1064 described above.

The optical sensor 1061 may be configured to capture images within a field of view of the optical sensor 1061. In this regard, the optical sensor 1061 may be a digital imaging device configured to receive, for example, light to capture an image and convert the light into data representative of the light captured by the optical sensor 1061. As mentioned above, the optical sensor 1061 may be embodied as or include a camera, a lidar sensor, a laser scanning sensor, or the like. According to some example embodiments, the optical sensor 1061 may be controlled by the processing circuitry 1010 to capture images as requested by the processing circuitry 1010. In this regard, the processing circuitry 1010 may be configured to cause images to be captured such that the images may be associated (e.g., overlapping images) to generate a larger image or model from component captured images. The optical sensor 1061 may be coupled to, for example, a helmet, such as helmet 102. According to some example embodiments, the optical sensor 1061 may be coupled to the display 1051. In this regard, the optical sensor 1061 and the display 1051 may maintain a known relative position between the field of view of the optical sensor 1061 and a field of view of the user to support presentation of augmented reality on the display 1051.

The sensor interface 1060 may also be operably coupled to the healthcare implement 1063. In this regard, the healthcare implement 1063 may be a tool or other device that a user may employ to perform a healthcare procedure (e.g., a diagnostic or treatment procedure). According to some example embodiments, the healthcare implement 1063 may be, for example, an ultrasound-imaging device, infrared imaging device, needles including a collapsed lung needle, probes, scalpel, forceps, scissors, endoscope, stethoscope, catheter, tube, bandage, or the like. According to some example embodiments, the healthcare implement 1063 may be an imaging sensor such as an ultrasound-imaging sensor (e.g., ultrasound-imaging sensor 230) configured to use sounds waves to perform imaging of the body or an internal organ (e.g., the heart). According to some example embodiments, the imaging sensor may be any type of imaging sensor that may be used in conjunction with predictive internal anatomy visualizations, such as, for example, infrared imaging sensors, portable X-ray, or the like.

In this regard, for example, as a needle, the healthcare implement 1063 may be used to treat a collapsed lung, perform a chest tube insertion, or gain intraosseous access with a sternal needle. Additionally, according to some example embodiments, a needle may employ a tip sensor (e.g., that depresses when contacted) and the needle may have communications capabilities to inform, for example, the processing circuitry 1010 that the needle has be used to perform a procedure.

According to some example embodiments, the processing circuitry 1010, may be configured to capture, via the optical sensor 1061, a plurality of body registration points on a body of an individual. Such body registration points may be used, not only for registration, but also for external anatomical measurements. Additionally, according to some example embodiments, the processing circuitry 1010 may be configured to receive a plurality of external anatomical measurements of the body. Such external anatomical measurements may be determined from, for example, the body registration points. Further, according to some example embodiments, the processing circuitry 1010 may be configured to apply the plurality of external anatomical measurements to a body shape model and determine an organ placement prediction for the body of the individual based on the application of the plurality of external anatomical measurements to the body shape model. In this regard, the organ placement prediction may be comprise organ position information, organ size information, and organ shape information for use to render a plurality of organs. Additionally, the processing circuitry 1010 is further configured to align the organ placement prediction with the plurality of body registration points for registration. Moreover, processing circuitry 1010 may be configured to render, on the display 1051, the organ placement prediction in alignment with the plurality of body registration points based on a position of the field of view of, for example, the optical sensor 1061 relative to the plurality of body registration points. In this regard, the organ placement prediction may be rendered in augmented reality as an augmented reality object or collection of objects that, for example, overlay, in the display 1051, a user's real-world view of the body of the individual. Alternatively, the organ placement prediction may be may be rendered in augmented reality such that the organ placement prediction is integrated with an image of the body of the individual provided on the display 1051.

As mentioned above, according to some example embodiments, the predictive internal anatomy visualization device 1000 may be embodied as a headset, such as the headset 100. In this regard, according to some example embodiments, the display 1051 and the optical sensor 1061 may be coupled to the headset 100 such that movement of the headset 100 by the user of the headset 100 moves both the display 1051 and the optical sensor 1061 and also changes the field of view of the optical sensor 1061. Further, according to some example embodiments, the plurality of external anatomical measurements applied to the body shape model to determine the organ placement prediction may include, for example, a shoulder-to-shoulder distance and a chest circumference. Additionally, according to some example embodiments, the processing circuitry 1010 may be further configured to receive an external shape estimation of a body and determine the organ placement prediction based on the external shape estimation by providing the body shape estimation to the body shape model for use and consideration in determining the organ placement prediction.

Further, according to some example embodiments, the processing circuitry 1010 may be configured to capture, via the optical sensor 1061, a registration point location of the plurality of body registration points by the following process. The processing circuitry 1010 may capture an image of the pointing implement 1052 positioned or pointing at the registration point location on the body of the individual. In this regard, the registration point location may be one of the plurality of body registration points that have been defined for registration of the organ placement prediction with the body. Additionally, the processing circuitry 1010 may be configured to develop a registration frame based on the plurality of body registration points including the registration point location and align the organ placement prediction with the plurality of body registration points by aligning the organ placement prediction with the registration frame.

Further, according to some example embodiments, the processing circuitry 1010 may be configured to capture a registration point location of the plurality of body registration points by capturing an image of the pointing implement 1052 positioned at the registration point location on the body of the individual in response to actuation of the capture switch 1053 by a user. Additionally, the processing circuitry 1010 may be further configured to receive an identification of the individual and/or a unique code associated with the individual. Moreover, the processing circuitry 1010 may be configured to receive the plurality of external anatomical measurements of the body of the individual in response to querying, using the identification and/or the unique code of the individual, a measurement dataset comprising external anatomical measurements for a plurality of individuals including the individual.

According to some example embodiments, the processing circuitry 1010 may be further configured to render guidance indicators (e.g., guidance indicators 246 and 248) on the display 1051 with the organ placement prediction. In this regard, the guidance indicators may provide the user with visual instructive information for positioning a body-aligned apparatus, such as, for example healthcare implement 1063 on the body of the individual. According to some example embodiments, the body-aligned apparatus may be a healthcare training tool or personal protective equipment. In this regard, the body-aligned apparatus may be embodied as a healthcare implement that is an imaging sensor such as an ultrasound-imaging sensor (e.g., ultrasound-imaging sensor 230). Further, according to some example embodiments, the body-aligned apparatus may be configured to capture position-based healthcare information associated with the body of the individual. In this regard, the processing circuitry 1010 may be further configured to adjust the alignment of the organ placement prediction based on the position-based healthcare information, and/or adjust the organ placement prediction based on the position-based healthcare information.

Figure 16:
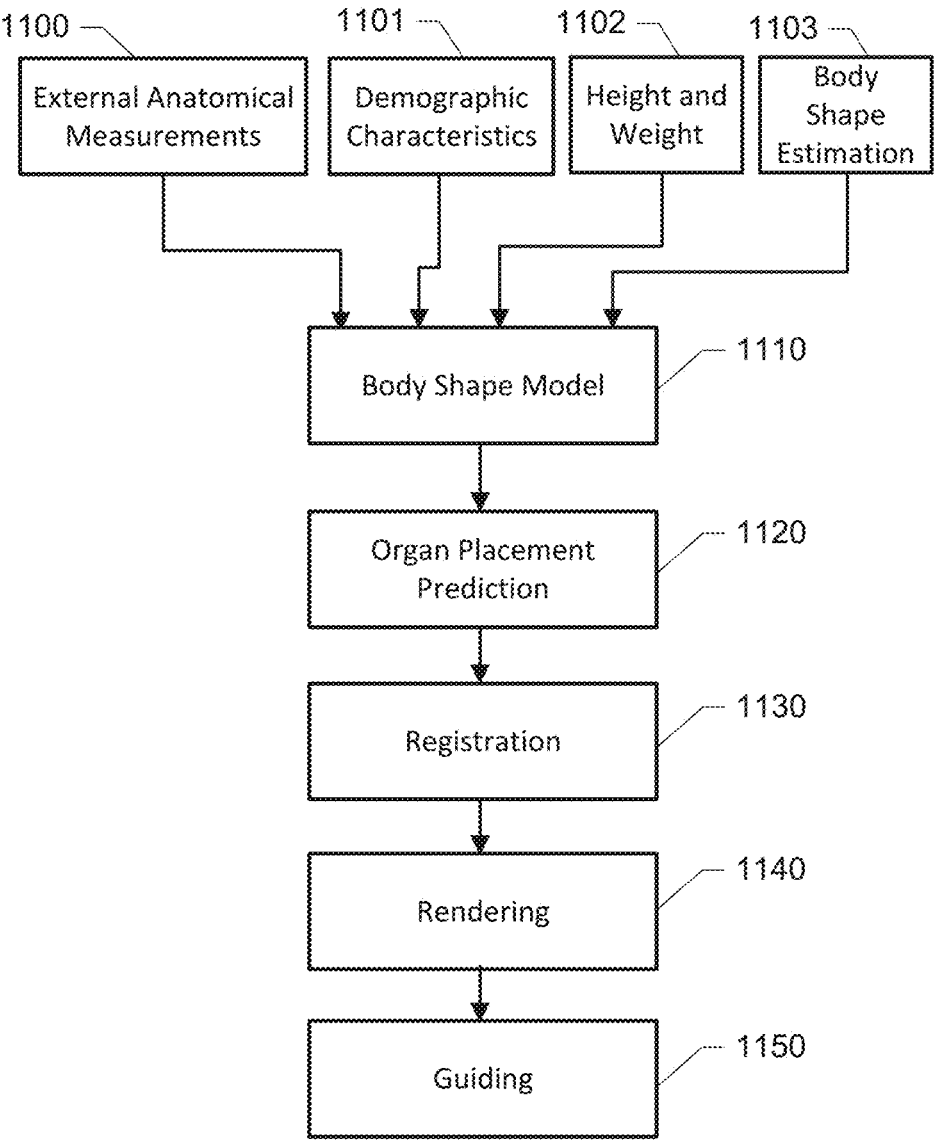
FIG. 16 illustrates a flowchart of a method for generating and rendering an organ placement prediction according to some example embodiments.

Now referring to FIG. 16, an example method for generating and rendering an organ placement prediction is shown in the form of a flowchart. In this regard, the method begins with various forms of inputs to be applied to the body shape model 1110. In this regard, the types of information that may be applied to the body shape model 1110 may include external anatomical measurements 1100, demographic characteristics 1101, height and weight 1102, and/or a body shape estimation 1103. According to some example embodiments, these inputs may be received by the processing circuitry 1010 and the processing circuitry 1010 may apply the inputs to the body shape model 1110 to generate an organ placement prediction 1120. According to some example embodiments, the inputs may be compared to corresponding dimensions of the body shape model 1110 and a multi-dimensional optimization may be performed to determine a highest confidence match between the inputs and the dimensions of the body shape model 1110. If a confidence score of the highest confidence match exceeds a confidence threshold, then the organ placement prediction 1120 associated with that high confidence match may be returned. In association with generating the organ placement prediction 1120, the processing circuitry 1010 may also perform a registration process to position the organ placement prediction 1120 in a proper position relative to the body. The registration process may comprise defining a plurality of body registration points on body that are used for alignment (e.g., in three dimensions) with corresponding model registration points of the organ placement prediction. Via this alignment, the organ placement prediction is registered to the body. According to some example embodiments, such registration 1130 may be maintained regardless of the movement of the user and the user's head. After the registration 1130 is performed, the organ placement prediction 1120 may be subjected to rendering 1140. In this regard, the organ placement prediction 1120 may be rendered in combination with real-world objects in an augmented reality implementation. Additionally, according to some example embodiments, guiding 1150 may be performed by providing indicators, such as arrows, on the organ placement prediction rendered on the display 1051. Such indicators may guide the user in positioning, for example, a healthcare tool for a procedure or for training.

Now referring to FIG. 17, a flowchart of an example method for implementing internal anatomy visualization in augmented reality is provided. In this regard, the example method may comprise, at 1200, capturing, via an optical sensor, a plurality of registration point locations on a body of an individual. Additionally, at 1210, the example method may comprise receiving a plurality of external anatomical measurements of the body, for example, by the processing circuitry 1010.

At 1220, the example method may comprise applying the plurality of external anatomical measurements to a body shape model and, at 1230, determining an organ placement prediction for the body of the individual based on the application of the plurality of external anatomical measurements to the body shape model. According to some example embodiments, the organ placement prediction may comprise organ position information, organ size information, and organ shape information for a plurality of organs. The example method may also comprise, at 1240, aligning the organ placement prediction with the plurality of registration point locations, and, at 1250, rendering, on a display, the organ placement prediction in alignment with the plurality of registration point locations based on a position of a sensor field of view of the optical sensor relative to the plurality of registration point locations. According to some example embodiments, the organ placement prediction may be rendered as an augmented reality object that overlays a user's real-world view of the body of the individual or is integrated with an image of the body of the individual provided on the display.

According to some example embodiments, the plurality of external anatomical measurements may include shoulder-to-should distance and a chest circumference of the body of the individual. Additionally or alternatively, according to some example embodiments, capturing a registration point location of the plurality of registration point locations may comprise capturing an image of a pointing implement positioned at the registration point location on the body of the individual. In this regard, the registration point location may be one of the plurality of registration point locations. Additionally, the example method may comprise developing a registration frame based on the plurality of body registration points including the registration point location. In this regard, aligning the organ placement prediction with the plurality of body registration points may comprise aligning the organ placement prediction with the registration frame.

Additionally or alternatively, according to some example embodiments, capturing a registration point location of the plurality of body registration points may comprise capturing an image of a pointing implement positioned at a registration point location on the body of the individual in response to actuation of a capture switch by a user. Additionally or alternatively, according to some example embodiments, the example method may further comprise rendering guidance indicators on the display with the organ placement prediction, the guidance indicators providing a user with visual instructive information for positioning a body-aligned apparatus on the body of the individual.

As used herein, the term "module" is intended to include a computer-related entity, such as but not limited to hardware, software, or a combination of hardware and software. For example, a module may be, but is not limited to being a software or hardware implementation of a process, an object, an executable, and/or a thread of execution, which may be implemented via a processor or computer. By way of example, both an application running on a computing device and/or the computing device can be a module. One or more modules can reside within a process and/or thread of execution and a module may be localized on one computer and/or distributed between two or more computers. In addition, these modules can execute from various computer readable media having various data structures stored thereon. The modules may communicate by way of local and/or remote processes such as in accordance with a signal having one or more data packets, such as data from one module interacting with another module in a local system, distributed system, and/or across a network such as the Internet with other systems by way of the signal. Each respective module may perform one or more functions that will be described in greater detail herein. However, it should be appreciated that although such example is described in terms of separate modules corresponding to various functions performed, some examples need not necessarily utilize modular architectures for employment of the respective different functions. Thus, for example, code may be shared between different modules, or the processing circuitry itself may be configured to perform all of the functions described as being associated with the modules described herein. Furthermore, in the context of this disclosure, the term "module" should not be understood as a nonce word to identify any generic means for performing functionalities of the respective modules. Instead, the term "module" should be understood to be a modular entity that is specifically configured in, or can be operably coupled to, processing circuitry to modify the behavior and/or capability of the processing circuitry based on the hardware and/or software that is added to or otherwise operably coupled to the processing circuitry to configure the processing circuitry accordingly.

Many modifications and other embodiments of the invention set forth herein will come to mind to one skilled in the art having the benefit of the teachings presented in the foregoing descriptions and the associated drawings. Therefore, it is to be understood that embodiments of the invention are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements or functions, it should be appreciated that different combinations of elements or functions may be provided by alternative embodiments without departing from the scope of the appended claims. In this regard, for example, different combinations of elements or functions than those explicitly described above are also contemplated as may be set forth in some of the appended claims. In cases where advantages, benefits or solutions to problems are described herein, it should be appreciated that such advantages, benefits or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

That which is claimed:

1. An anatomy visualization device comprising:

a display;

an optical sensor coupled to the display such that the optical sensor and the display maintain a known relative position to support presentation of augmented reality on the display, the optical sensor having a sensor field of view; and processing circuitry configured to:

capture, via the optical sensor, a plurality of body registration points on a body of an individual;

receive a plurality of external anatomical measurements of the body;

apply the plurality of external anatomical measurements to a body shape model;

determine an organ placement prediction for the body of the individual based on application of the plurality of external anatomical measurements to the body shape model, the organ placement prediction comprising organ position information, organ size information, and organ shape information for a plurality of organs;

align the organ placement prediction with the plurality of body registration points; and render, on the display, the organ placement prediction in alignment with the plurality of body registration points based on a position of the sensor field of view relative to the plurality of body registration points, wherein the organ placement prediction is rendered as an augmented reality object that overlays a user's real-world view of the body of the individual or is integrated with an image of the body of the individual provided on the display.

2. The anatomy visualization device of claim 1 further comprising a headset, wherein the display and the optical sensor are coupled to the headset such that movement of the headset by a user moves the display and the optical sensor, and changes the sensor field of view.

3. The anatomy visualization device of claim 1, wherein the plurality of external anatomical measurements include shoulder-to-shoulder distance and a chest circumference.

4. The anatomy visualization device of claim 1, wherein the processing circuitry is further configured to receive an external shape estimation of the body; and wherein the processing circuitry is further configured to determine an organ placement prediction based on the external shape estimation.

5. The anatomy visualization device of claim 1, wherein the processing circuitry is configured to capture a registration point location of the plurality of body registration points by:

capturing an image of a pointing implement positioned at the registration point location on the body of the individual, the registration point location being one of the plurality of body registration points; and developing a registration frame based on the plurality of body registration points including the registration point location, wherein the processing circuitry is configured to align the organ placement prediction with the plurality of body registration points by aligning the organ placement prediction with the registration frame.

6. The anatomy visualization device of claim 1 further comprising a pointing implement comprising a capture switch, wherein the processing circuitry is configured to capture a registration point location of the plurality of body registration points by capturing an image of the pointing implement positioned at the registration point location on the body of the individual in response to actuation of the capture switch by a user.

7. The anatomy visualization device of claim 1, wherein the processing circuitry is further configured to receive an identification of the individual, wherein the processing circuitry is configured to receive the plurality of external anatomical measurements of the body of the individual in response to querying, using the identification of the individual, a measurement dataset comprising external anatomical measurements for a plurality of individuals including the individual.

8. The anatomy visualization device of claim 1, wherein the processing circuitry is configured to render guidance indicators on the display with the organ placement prediction, the guidance indicators providing a user with visual instructive information for positioning a body-aligned apparatus on the body of the individual.

9. The anatomy visualization device of claim 8, wherein the body-aligned apparatus is an ultrasound imaging sensor.

10. The anatomy visualization device of claim 8, wherein the body-aligned apparatus is configured to capture position-based healthcare information associated with the body of the individual, wherein the processing circuitry is further configured to:

adjust the alignment of the organ placement prediction based on the position-based healthcare information, or adjust the organ placement prediction based on the position-based healthcare information.

11. The anatomy visualization device of claim 8, wherein the body-aligned apparatus is a healthcare training tool or personal protective equipment.

12. The anatomy visualization device of claim 1, wherein the body shape model comprises a statistically-constructed model that includes the organ position information, the organ size information, and the organ shape information linked with external anatomical measurements.

13. The anatomy visualization device of claim 1, wherein the processing circuitry is configured to apply of the plurality of external anatomical measurements and demographic characteristics to the body shape model to determine the organ placement prediction, the demographic characteristics comprising ethnicity, gender, or age.

14. A method for internal anatomy visualization in augmented reality comprising:

capturing, via an optical sensor, a plurality of body registration points on a body of an individual;

receiving, by processing circuitry, a plurality of external anatomical measurements of the body;

applying the plurality of external anatomical measurements to a body shape model;

determining an organ placement prediction for the body of the individual based on application of the plurality of external anatomical measurements to the body shape model, the organ placement prediction comprising organ position information, organ size information, and organ shape information for a plurality of organs;

aligning the organ placement prediction with the plurality of body registration points; and rendering, on a display, the organ placement prediction in alignment with the plurality of body registration points based on a position of a sensor field of view of the optical sensor relative to the plurality of body registration points, wherein the organ placement prediction is rendered as an augmented reality object that overlays a user's real-world view of the body of the individual or is integrated with an image of the body of the individual provided on the display.

15. The method of claim 14, wherein the plurality of external anatomical measurements include a shoulder-to-shoulder distance and a chest circumference.

16. The method of claim 14, wherein capturing a registration point location of the plurality of body registration points comprises:

capturing an image of a pointing implement positioned at the registration point location on the body of the individual, the registration point location being one of the plurality of body registration points; and developing a registration frame based on the plurality of body registration points including the registration point location, wherein aligning the organ placement prediction with the plurality of body registration points comprises aligning the organ placement prediction with the registration frame.

17. The method of claim 14 wherein capturing a registration point location of the plurality of body registration points comprises capturing an image of a pointing implement positioned at a registration point location on the body of the individual in response to actuation of a capture switch by a user.

18. The method of claim 14 further comprising rendering guidance indicators on the display with the organ placement prediction, the guidance indicators providing a user with visual instructive information for positioning a body-aligned apparatus on the body of the individual.

19. A headset device comprising:

a support element configured to be worn on a head of a user;

a display coupled to the support element and positioned to provide visual information to the user within a field of view of the user;

an optical sensor coupled to the support element such that the optical sensor and the display maintain a known relative position, the optical sensor having a sensor field of view that at least partially overlaps the field of view of the user beyond the display; and processing circuitry configured to:

capture, via the optical sensor, a plurality of body registration points on a body of an individual;

receive a plurality of external anatomical measurements of the body;

apply the plurality of external anatomical measurements to a body shape model;

determine an organ placement prediction for the body of the individual based on application of the plurality of external anatomical measurements to the body shape model, the organ placement prediction comprising organ position information, organ size information, and organ shape information for a plurality of organs;

align the organ placement prediction with the plurality of body registration points; and render, on the display, the organ placement prediction in alignment with the plurality of body registration points based on a position of the sensor field of view relative to the plurality of body registration points, wherein the organ placement prediction is rendered as an augmented reality object that overlays a user's real-world view of the body of the individual or is integrated with an image of the body of the individual provided on the display.

20. The headset device of claim 19, wherein the processing circuitry is configured to render guidance indicators on the display with the organ placement prediction, the guidance indicators providing a user with visual instructive information for positioning a body-aligned apparatus on the body of the individual.

* * * * *